US010434006B2

(12) United States Patent
Füglister

(10) Patent No.: US 10,434,006 B2
(45) Date of Patent: Oct. 8, 2019

(54) TONGUE DEFORMATION IMPLANT

(71) Applicant: Fabian Hermann Urban Füglister, Würenlos (CH)

(72) Inventor: Fabian Hermann Urban Füglister, Würenlos (CH)

( * ) Notice: Subject to any disclaimer, the term of this patent is extended or adjusted under 35 U.S.C. 154(b) by 35 days.

(21) Appl. No.: 14/405,442

(22) PCT Filed: Jun. 7, 2013

(86) PCT No.: PCT/IB2013/001195
§ 371 (c)(1),
(2) Date: Dec. 4, 2014

(87) PCT Pub. No.: WO2013/182893
PCT Pub. Date: Dec. 12, 2013

(65) Prior Publication Data
US 2015/0164681 A1    Jun. 18, 2015

Related U.S. Application Data

(60) Provisional application No. 61/787,006, filed on Mar. 15, 2013, provisional application No. 61/656,582, filed on Jun. 7, 2012.

(51) Int. Cl.
*A61F 5/56* (2006.01)

(52) U.S. Cl.
CPC .................... *A61F 5/566* (2013.01)

(58) Field of Classification Search
CPC .... A61F 5/56; A61F 5/556; A61F 5/58; A61F 2/20; A61F 2/206; A61F 2/88; C22F 1/006; A61B 5/15117

(Continued)

(56) References Cited

U.S. PATENT DOCUMENTS 5,226,979 A * 7/1993 Thoma .................... C22F 1/006
148/402
5,716,410 A * 2/1998 Wang ........................ A61F 2/88
604/531

(Continued)

FOREIGN PATENT DOCUMENTS

CN            1717208 A       1/2006

OTHER PUBLICATIONS

China Patent Office, Official Action for Related case CN201380042313.7, dated Sep. 29, 2015, SIPO, P.R.C.

*Primary Examiner* — Keri J Nelson
*Assistant Examiner* — Adam Baker
(74) *Attorney, Agent, or Firm* — Babcock IP, PLLC

(57) ABSTRACT

A method and apparatus for the treatment of OSA are disclosed which protrudes the tongue and hence enlarges the pharyngeal cross-sectional area by implanting a state changing actuator, one leg inserted helically directly into the root of the tongue near the hyoid bone, along and near the base of the tongue into the body of the tongue, the section leaving the root of the tongue providing a torque (tending to expand the V-shape of the implant), the other leg acting as a force distribution placed between the root of the tongue and the geniohyoid, or between geniohyoid and mylohyoid. Another embodiment shows placement of a passive implant to permanently compress the tongue by deforming it providing a force compressing the tongue, the force directed toward the axis of the helix, hence protruding the tongue to enlarge the pharyngeal cross-sectional passageway to prevent obstructions of the airway.

26 Claims, 23 Drawing Sheets

(58) Field of Classification Search
USPC .......................................... 128/848; 148/402
See application file for complete search history.

(56) References Cited

U.S. PATENT DOCUMENTS

| | | | |
|---|---|---|---|
| 6,019,779 A * | 2/2000 | Thorud | A61F 2/88 606/198 |
| 8,167,787 B2 * | 5/2012 | Gillis | A61F 5/566 128/848 |
| 8,186,355 B2 * | 5/2012 | van der Burg | A61B 17/0401 128/848 |
| 8,327,854 B2 * | 12/2012 | Gillis | A61F 5/56 128/848 |
| 8,800,567 B2 * | 8/2014 | Weadock | A61F 2/00 128/846 |
| 2007/0246052 A1 | 10/2007 | Hegde et al. | |
| 2008/0066765 A1 | 3/2008 | Paraschac et al. | |
| 2008/0071356 A1 * | 3/2008 | Greenhalgh | A61B 17/8858 623/1.16 |
| 2008/0208265 A1 | 8/2008 | Frazier et al. | |
| 2009/0173351 A1 * | 7/2009 | Sahin | A61F 2/02 128/848 |
| 2009/0177027 A1 * | 7/2009 | Gillis | A61F 5/56 600/37 |
| 2011/0100376 A1 * | 5/2011 | Rousseau | A61F 5/566 128/848 |
| 2011/0100378 A1 | 5/2011 | Rousseau | |
| 2012/0312307 A1 * | 12/2012 | Paraschac | A61F 5/566 128/848 |

* cited by examiner

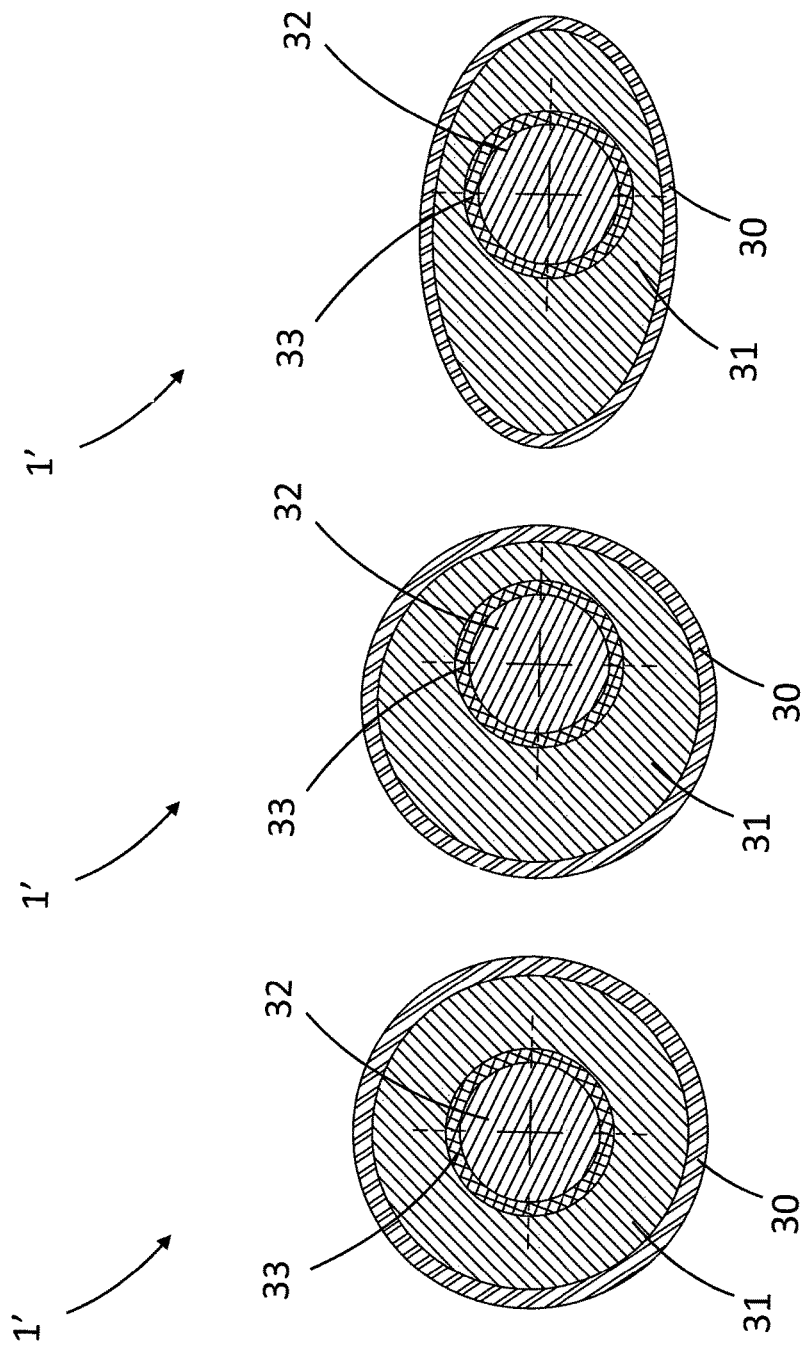

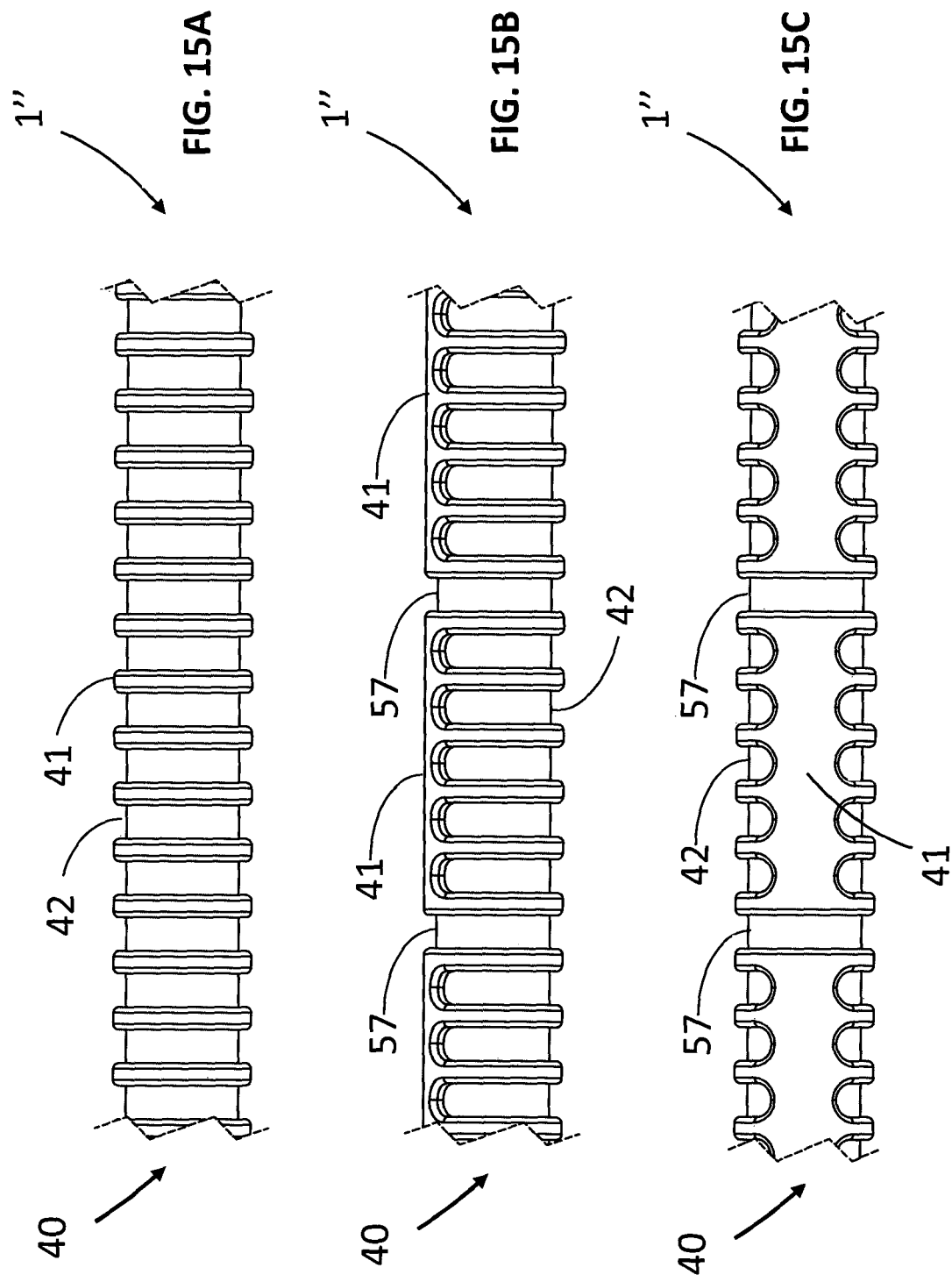

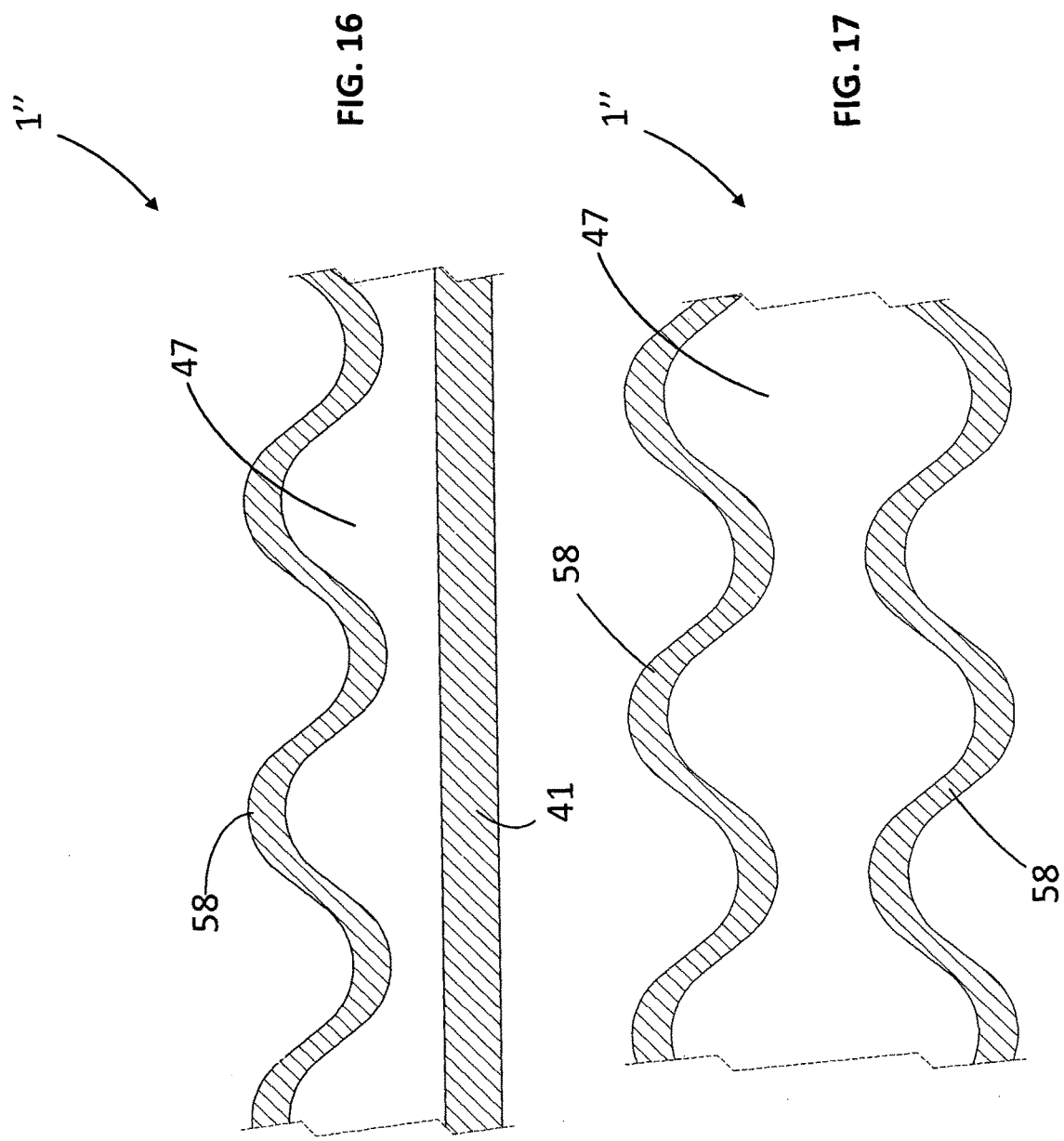

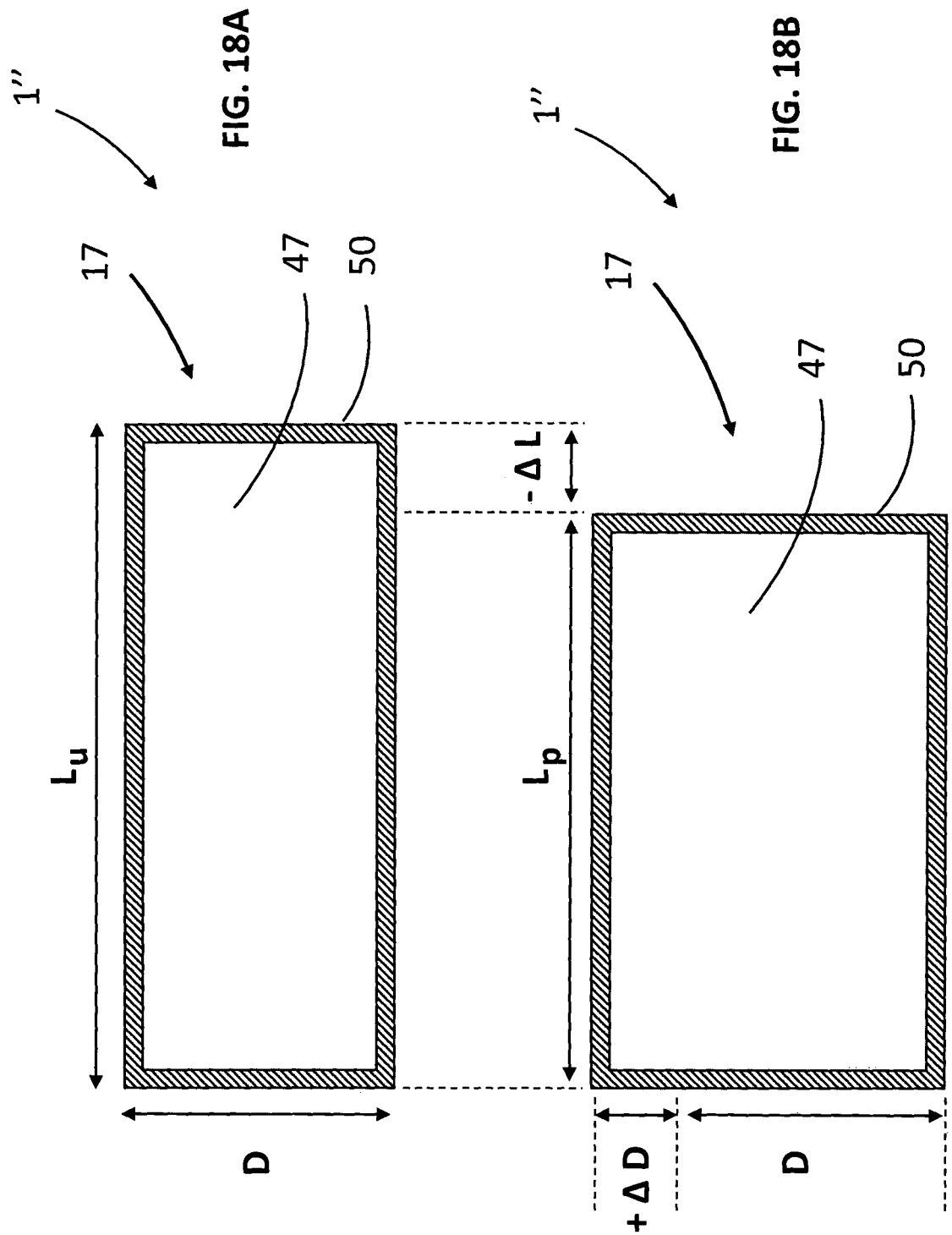

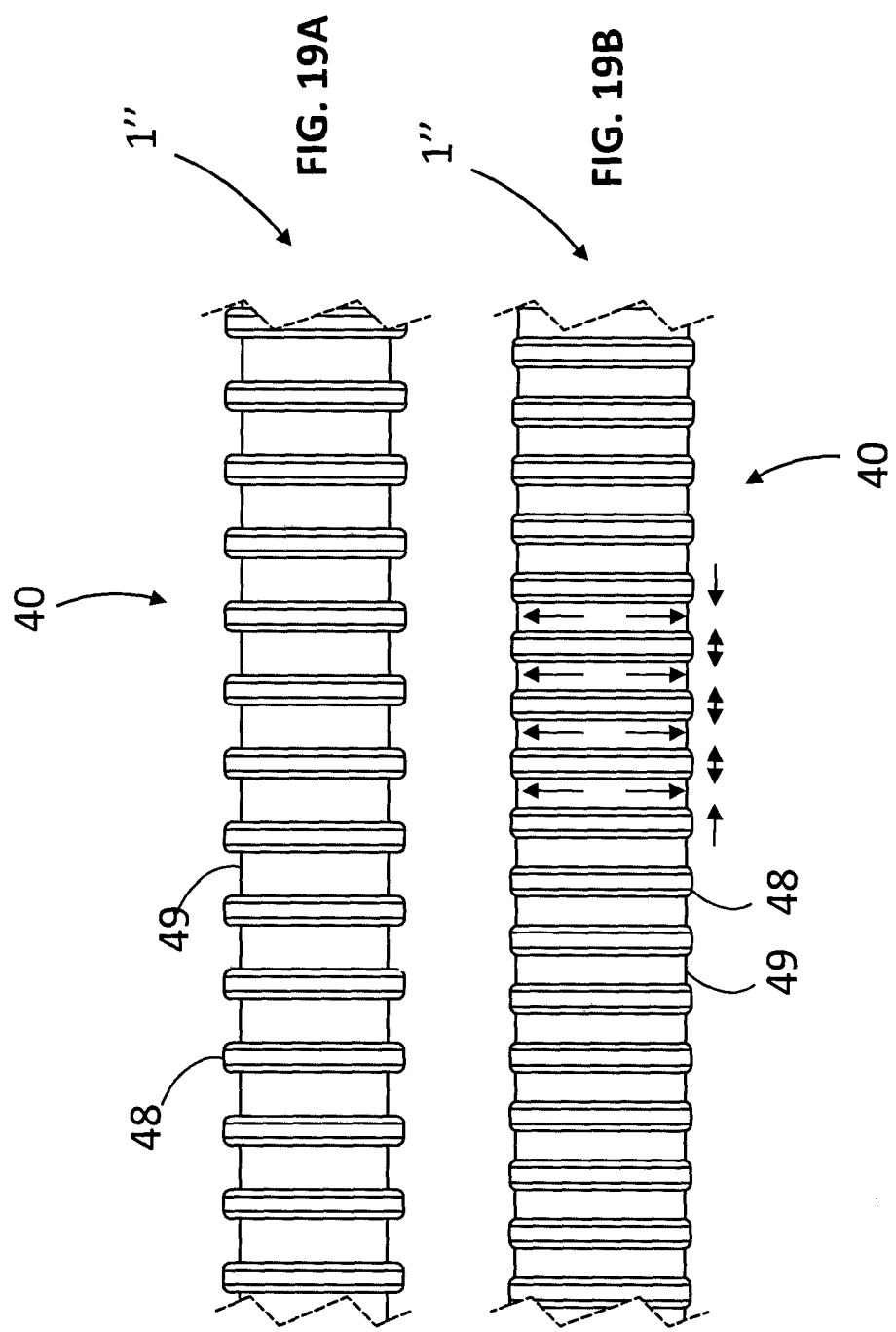

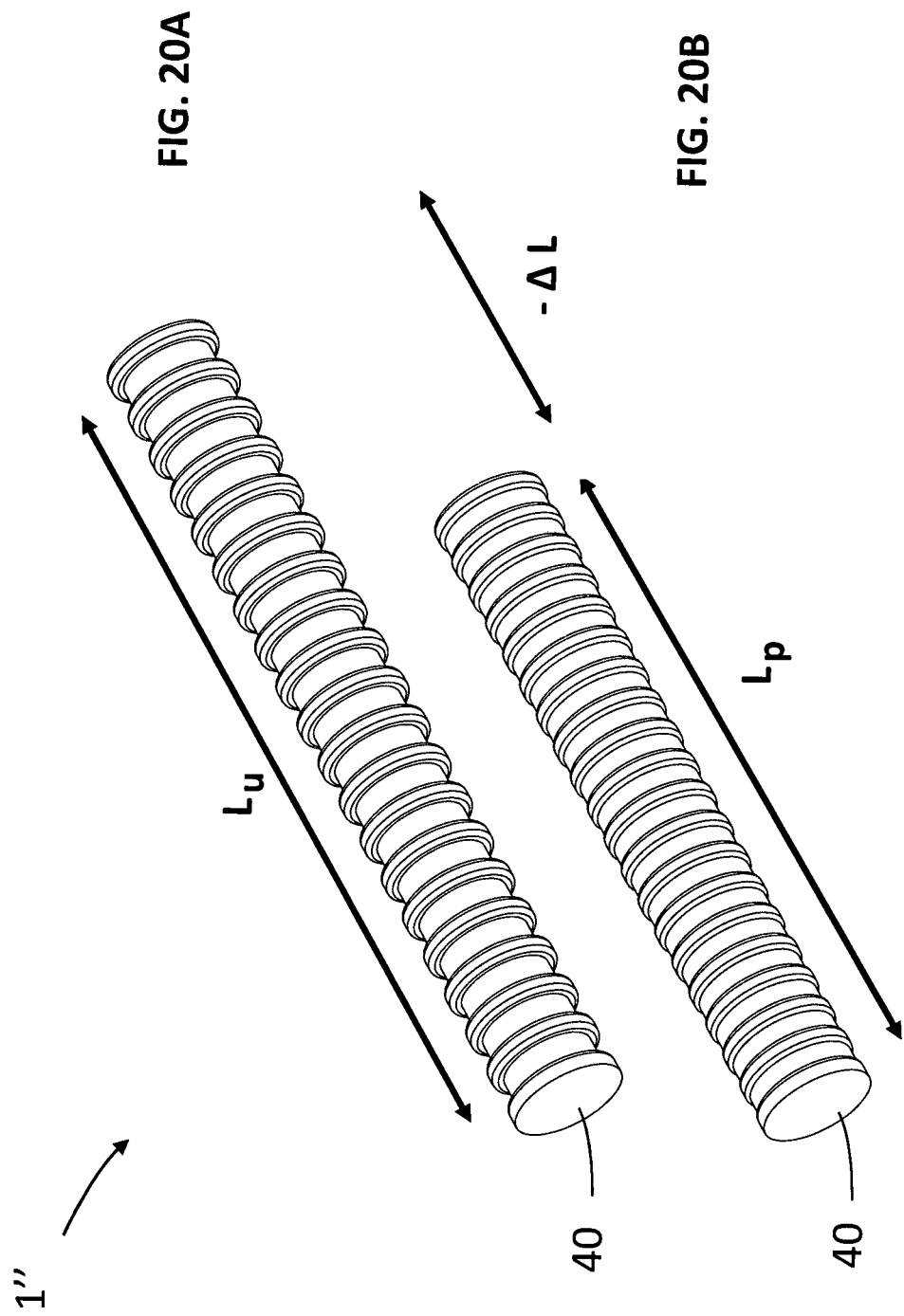

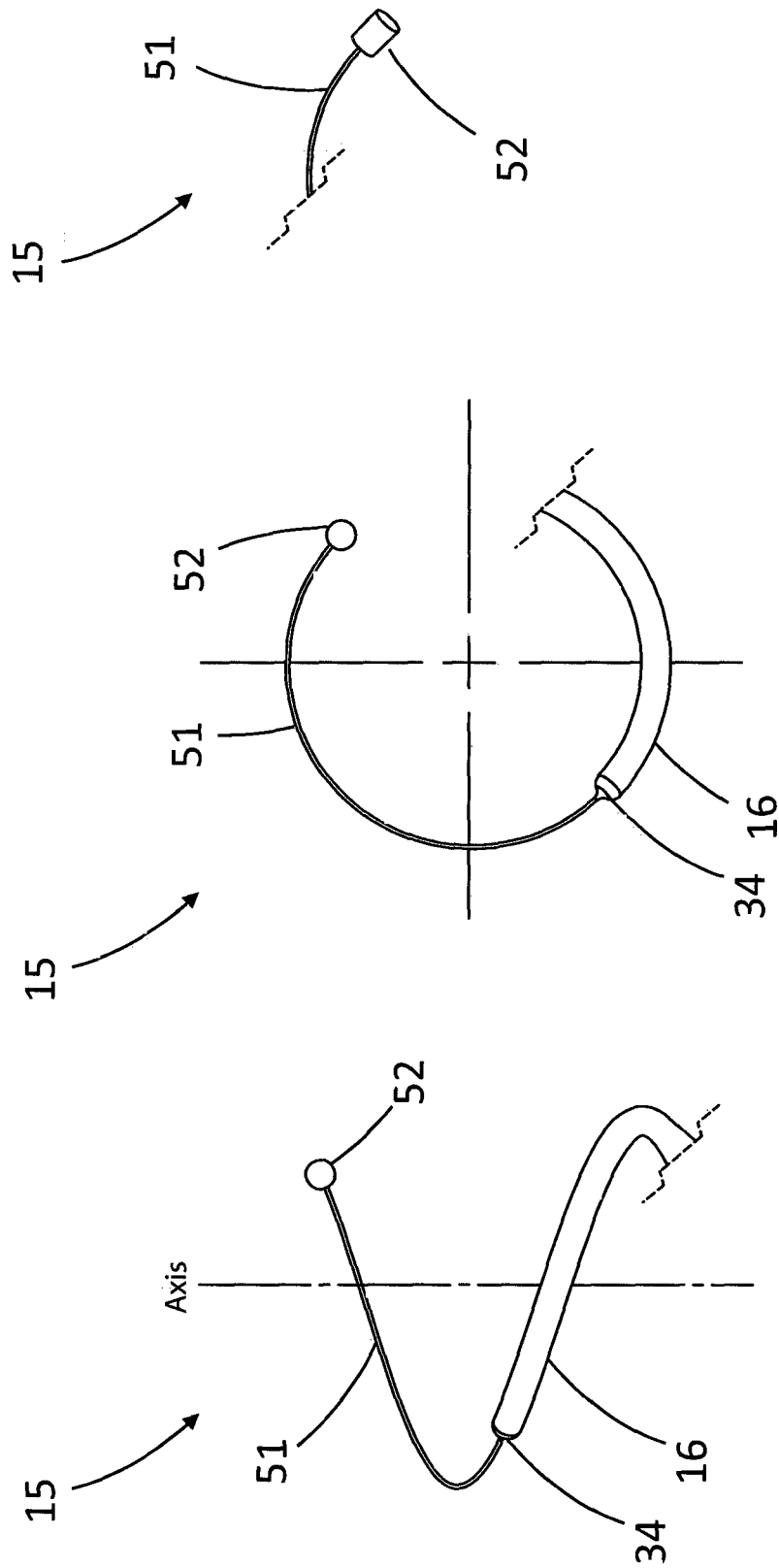

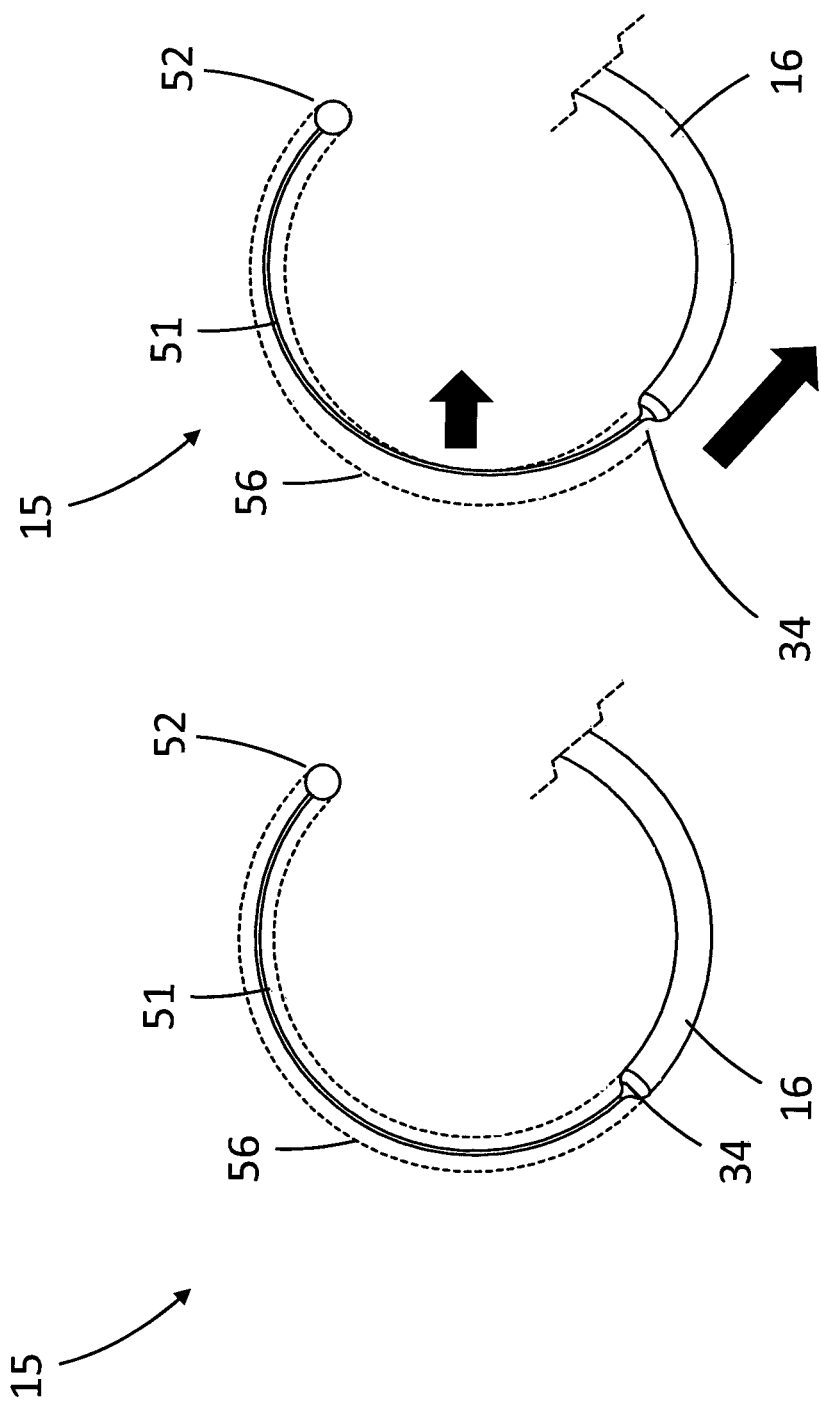

TONGUE DEFORMATION IMPLANT

CROSS REFERENCE TO RELATED APPLICATIONS

This application is the National Stage of International Application No. PCT/IN2013/001195, filed Jun. 7, 2013, which claims benefit under 35 USC § 119(a), to U.S. patent application Ser. No. 61/656,582, filed Jun. 7, 2012 and to U.S. patent application Ser. No. 61/787,006, filed Mar. 15, 2013.

COPYRIGHT & LEGAL NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. Further, no references to third party patents or articles made herein are to be construed as an admission that the present invention is not entitled to antedate such material by virtue of prior invention.

FIELD OF THE INVENTION

The present invention relates generally to the treatment of obstructive sleep apnea and snoring.

BACKGROUND OF THE INVENTION

Obstructive sleep apnea (OSA) is defined as recurrent cessation of breathing with upper airway obstruction occurring during sleep, resulting in substantially reduced (hypopnea) or complete cessation (apnea) of airflow despite ongoing breathing efforts. By convention, the patient must experience more than 30 episodes lasting more than 10 seconds or more than five abnormal breathing disturbances (hypopneas or apneas) per hour of sleep. In most cases the person is unaware that a disturbance is taking place. Referring now to FIG. 1, the human upper airway anatomy consists of the mandible bone 12, tongue 2, pharynx 3, hyoid bone 4, palate 5, uvula 6, epiglottis 7, lips 8, larynx 9, geniohyoid 10, mylohyoid 11, and adjacent facial structures. This anatomy plays a central role in speaking, breathing, mastication and swallowing. The airway is composed of numerous muscles and soft tissue but lacks rigid or bony support. Most notably, it contains a collapsible portion that extends from the hard palate 5 to the larynx 9. Although the ability of the upper airway to change shape and momentarily close is essential for speech and swallowing during an awake state, this feature also provides the opportunity for collapse at inopportune times such as during sleep. Although non-obese individuals may suffer from OSA, obesity is the main epidemiologic risk factor. It can influence both the structure[1] and function[2] of skeletal muscles. The interplay and correlated movements between all the anatomical structures is complex. These various physiological traits and the potential for each to influence sleep apnea pathophysiology have been described in detail in review articles[3]. The pathophysiological causes of OSA likely vary considerably between individuals. Important components likely include upper airway anatomy, the ability of the upper airway dilator muscles to respond to respiratory challenge during sleep, the propensity to wake from increased respiratory drive during sleep (arousal threshold), the stability of the respiratory control system (loop gain), and the potential for state-related changes in lung volume to influence these factors. Ultimately, the maintenance of pharyngeal patency depends on the equilibrium between occluding and dilating forces[4]. Upper airway dilator muscle activity is crucial to the counteraction of the negative intraluminal pressure generated in the pharynx during inspiration. Diminution of this activity during sleep is thought to play a central role in pharyngeal collapse and obstruction in patients with OSA.[5]

[1] Wade et al. (1990)
[2] Schwartz et al. (1998)
[3] White (2005)(2006), Schwab (1995)
[4] Douglas et al. (1994), Young et al. (1993)
[5] Remmers et al. (1978), Block et al. (1984) White (2006), Guilleminault et al. (1976)

The development of occlusion in this disorder has been related to "prolapsed" of the tongue into the pharynx. The tongue being prolapsed has been attributed to diminished neuromuscular activity in the genioglossus muscle inside the tongue which protrudes it forward, when it is activated.[6] Activation of the genioglossus (GG), the main tongue protrudor, has been shown to reduce pharyngeal resistance and collapsibility by far more than all other upper airway dilators.

[6] Remmers et al

There are a variety of treatments for OSA, but continuous positive airway pressure (CPAP), in which a nose mask is attached via a tube to a machine to blow pressurized air into the pharynx and push the collapsed section open, is still the gold standard in the treatment. Surgical procedures aiming for tissue reduction or stiffening to widen the pharynx have proven to be unreliable or to have adverse effects. However, as most patients dislike or refuse to use a mask for CPAP treatment, a new procedure involving implants are needed. Multiple trials attempting to relieve OSA by functional electric stimulation of upper airway dilators during sleep resulted in modest and/or inconsistent results.[7] Numerous attempts have been made towards treating OSA by placing implants into the tongue and are known in prior art, for example, the Pavad Medical tongue stabilization device U.S. Pat. Nos. 7,909,037 and 7,909,038, both dated Mar. 22, 2011. Another implant for treating OSA of is the Restore Medical implant disclosed in U.S. Pat. No. 7,401,611 dated Jul. 22, 2008, or the Revent Medical implant disclosed in U.S. Pat. No. 8,167,787 dated May 1, 2012 and U.S. Pat. No. 8,327,854 dated Dec. 11, 2012. All of the mentioned patents involve surgical procedures, which may not be suitable for some patients and/or which are extremely time consuming for inserting.

[7] Edmonds et al. (1992), Miki et al. (1989), Decker et al. (1993), Eisele et al. (1997), Guilleminault et al. (1995), Schnall et al. (1995), Schwartz et al. (1996), Oliven et al. (2001, 2003, 2007); Eastwood et al. (2003)

What is needed therefore is a surgically fast and minimally invasive tongue implant to treat OSA, which can deform like the tongue to comply with physiological tasks, but changing its rigidity to reliably and safely open up the pharyngeal airway blocked by the tongue by deforming it and providing a torque. The implant should stiffen the tongue along the base of the tongue and protrude it. Furthermore, it must minimize relative movement between implanted member and surface area in contact with the tongue to avoid abrasion of the implant.

SUMMARY OF THE INVENTION

A method and apparatus for the treatment of OSA are disclosed which protrudes the tongue and hence enlarges the pharyngeal cross-sectional area by implanting a state changing actuator, one leg inserted helically directly into the root of the tongue near the hyoid bone, along and near the base of the tongue into the body of the tongue, the section leaving the root of the tongue providing a torque (tending to expand the V-shape of the implant), the other leg acting as a force distribution placed between the root of the tongue and the geniohyoid, or between geniohyoid and mylohyoid. Another embodiment shows placement of a passive implant to permanently compress the tongue by deforming it providing a force compressing the tongue, the force directed toward the axis of the helix, hence protruding the tongue to enlarge the pharyngeal cross-sectional passageway to prevent obstructions of the airway.

BRIEF DESCRIPTION OF THE DRAWINGS

FIGS. 9A-9C show a cross section B-B of the helical section as indicated in FIG. 9

FIG. 15A shows a front view of another helical section of the fluid actuator FIG. 15B shows a side view of another helical section of the fluid actuator FIG. 15C shows a back view of another helical section of the fluid actuator FIG. 16 shows another cross section of a bending fluid actuator of the helical section with one wall designed to bend like an accordion bellows FIG. 17 shows another cross section of an expanding fluid actuator for widening portion, the walls designed to expand like an accordion bellows FIG. 18A is a schematic longitudinal cross section of the mandibulohyoid section of the fluid actuator in unpressurized state FIG. 18B is a schematic longitudinal cross section of the mandibulohyoid section of the fluid actuator in pressurized state FIG. 19A is a front view of another mandibulohyoid section of the fluid actuator in unpressurized state FIG. 19B is a front view of another mandibulohyoid section of the fluid actuator in pressurized state FIG. 20A is a perspective view of another mandibulohyoid section of the fluid actuator in unpressurized state FIG. 20B is a perspective view of another mandibulohyoid section of the fluid actuator in pressurized state FIGS. 21A-21C show different views of the flexible distal end section FIGS. 22A-22B show the distal end section under reacting to a small dislocation of the distal end of the helical section inside the tissue

DETAILED DESCRIPTION OF THE PREFERRED EMBODIMENT

Figure 1:
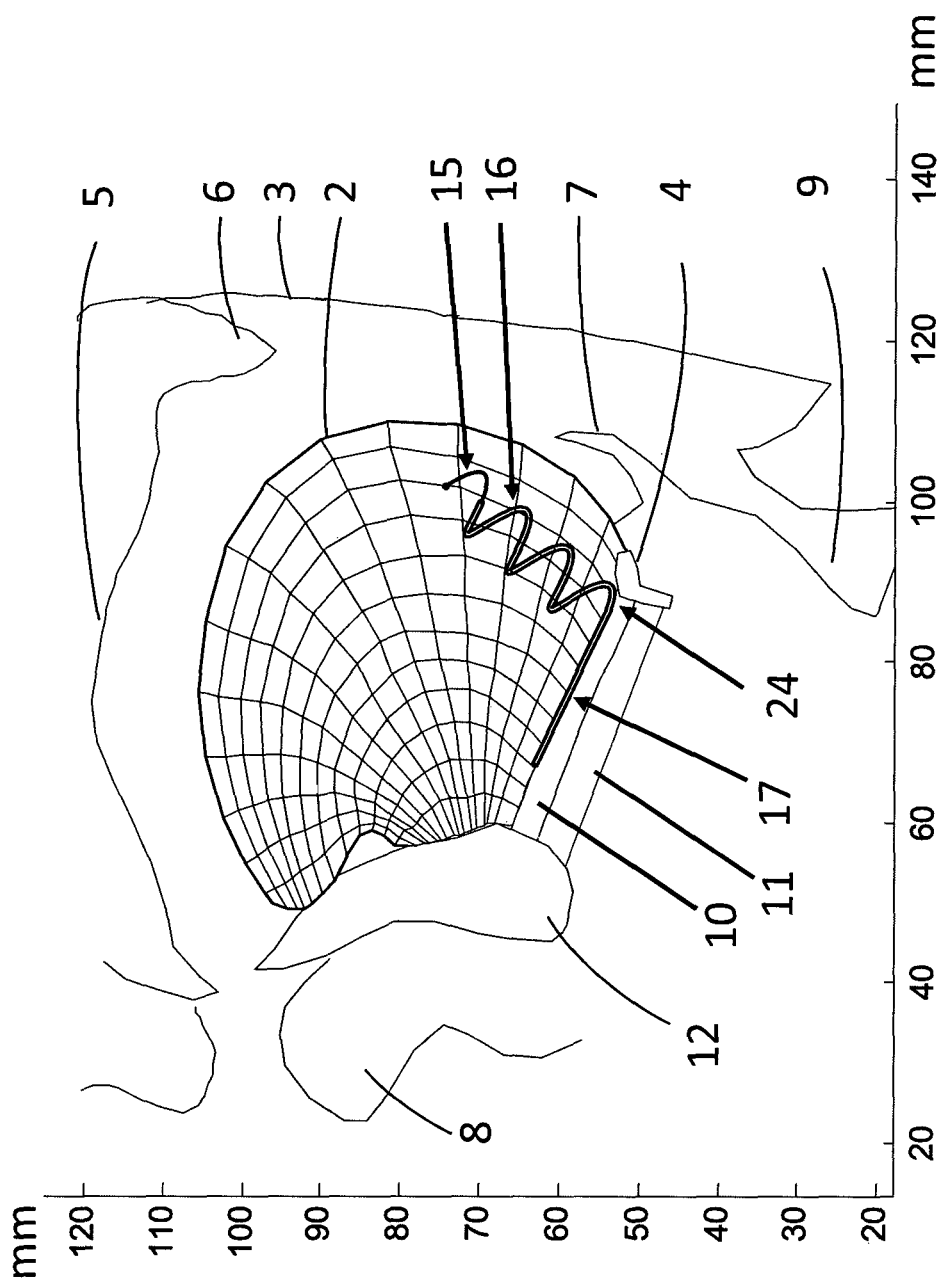
FIG. 1 is a midsagittal plane view of the pharynx with an implant helically inside the tongue and the force distribution section between root of the tongue and geniohyoid muscle.

The following descriptions are of exemplary embodiments of the invention and the inventors' conception of the best mode and are not intended to limit the scope, applicability or configuration of the invention in any way. Rather, the following description is intended to provide convenient illustrations for implementing various embodiments of the invention. As will become apparent, changes may be made in the function and/or arrangement of any of the elements described in the disclosed exemplary embodiments without departing from the spirit and scope of the invention.

The tongue is a unique and complex motor organ in the human body, but highly constrained inside the mouth. Its base is attached to the mandible and to the hyoid bone, while its upper and lateral surfaces are often in contact with the palate and the teeth. It is composed almost entirely of muscle and containing no skeleton. There are two different types of tongue muscles: intrinsic fibers, which originate and terminate within the tongue, and extrinsic fibers, those which arise externally from rigid bony surfaces. A detailed anatomical study has been described in Takemoto (2001). Activities of these muscles result in subtle movements of muscular structure and produce large deformations of the tongue's soft tissues. This is crucial for multiple physiological tasks, such as speech, mastication and swallowing. In speech, the tongue assumes stereotyped configurations which determine overall vocal tract shape, whereas in mastication and swallowing, the tongue acts to contain and propel a bolus of food. In each instance, regional activation of specific lingual muscles results in prototypical tissue deformation.

Tissue incompressibility is commonly assumed as the tissue is highly aqueous, giving the tongue its capability to behave as a muscular hydrostat, which is an organ, whose musculature creates motion and supplies skeletal support for that motion as well (like the elephant trunk or squid tentacle).[8] This incompressibility enables quick and efficient alteration of its form while maintaining original volume. Because of the complexity of lingual anatomy and its material attributes, the relationship between tongue structure and mechanical function is difficult to understand. Owing to incompressibility and complex fiber structure, lingual mechanics cannot be readily studied from changes of overall tissue shape. It requires an analysis of the complex organization of the human tongue musculature and internal muscle dynamics to understand the occurring deformations of the tongue, which is a necessary and critical requirement in order to fully understand the scope of this invention for a permanently implanted tongue actuator or a passive tongue compressing implant to treat OSA. Biomechanical models of the tongue and vocal tract have been in use since the 1960's to study articulation. Their complexity has increased with the acquisition of new knowledge about anatomical, neurophysiological and physical characteristics of the tongue, as well as with the vast growth in the computational capacities. All these models have significantly contributed to the increase in knowledge about tongue behavior and tongue control during speech production, and more specifically about the relations between muscle recruitments and tongue shape or acoustic signal (see in particular for 2D models Perkell, 1996, using his model presented in Perkell (1974); Kiritani et al., 1976, Dang and Honda, 2004; Hashimoto and Suga, 1986; Payan and Perrier, 1997; Sanguineti et al., 1998; For 3D models, see Buchaillard, S., Perrier, P., Payan, Y., 2009; Wilhelms-Tricarico, 1995; Kakita et al., 1985)

[8] Napadow 2002, a biomechanical model for sagittal tongue bending; Smith & Kier, 1989; Chiel, H. J., Carago, P., Mansour, J., Hathi, K., 1992, "Biomechanics of a Muscular Hydrostat: A Model of Lapping by a Reptilian Tongue," Biol. Cybern., 67, pp. 403-415. Wilhelms-Tricarico, R., 1995, "Physiological Modeling of Speech Production: Methods for Modeling Soft Tissue Articulators," J. Acoust. Soc. Am., 97, pp. 3085-3098.

The tongue implant should not limit movements in absolute terms like hyoid or tongue suspension for the treatment of OSA do, nor should it negatively influence speaking, mastication or swallowing. Out of these three tasks, not to influence speaking is the most difficult to cope with when placing an artificial member directly into the tongue. The production of speech involves complex muscles patterns. Some of these patterns are very fast, e.g. from a vowel to [k] about 30 ms[9], but doesn't involve strong muscle activation. Levels of forces generated by real speakers produced by the main muscles are in between 0.5 and 1.5 $N^{10}$. It must be noted, that these values measured are the force resultant. Inside the tongue accumulated forces are higher due to hydrostatic function of the tongue (Buchaillard and Perrier 2009)[11]. Since the production of speech is the fastest task with the lowest force production resultant, any device put directly into the tongue may create too much rigidity making it harder for the tongue to deform.

[9] Perrier et al. (2003). p. 10, table I
[10] Bunton, K., and Weismer, G. (1994)
[11] Table I for force generation capacities and table II for force levels (in Newton) observed for every tongue and mouth floor muscle during the production of vowels Other muscles activities, mainly mastication and swallowing, are deformations with stronger muscle activation. If the device makes swallowing or mastication movements harder in terms of necessary deformation forces, the increase would not be noted as easily or felt discomforting, because of stronger and slower muscle activation than in the production of speech. Regarding force levels, force distribution and deformations, these findings are essential to develop an implant to be placed directly inside the muscles of the tongue. The device must neither restrict movements of the tongue nor make speaking noticeably harder.

To simplify the complexity of the deformation analysis as well as to enhance the visual understanding, the 2D tongue deformation model of Perrier et al. (2003) has been chosen representing tongue characteristics that are relevant for speech and not the latest 3D models. Limiting the tongue model to the midsagittal plane is an acceptable simplification. In 2002 Badin et al. stated that «most 3D geometry of tongue, lips and face can be—at least for speech—predicted from their midsagittal contours.»[12] It was verified in 2006 as Badin and Serrurier teach that "The error made in the prediction of the 3D tongue shapes from their midsagittal contours can finally be quantified by the difference between the overall full 3D RMS errors for the model (0.22 cm) and for the inversion based on the midsagittal error (0.25 cm): the mere 0.03 cm (13.6%) increase of this error testifies to the very good predictability of the 3D tongue surface mesh from its 2D midsagittal contour."[13]

[12] Badin, P. & Serrurier, A. (2006). Three-dimensional linear modeling of tongue Articulatory data and models. Proceedings 7th Int. Seminar on Speech Production, ISSP7, pp. 395-402. p. 400
[13] P. 401

Accounting for tissue incompressibility would require measuring tissue deformations in 3D space, which obviously can't be done in a planar model. For that reason, tongue deformations in the direction orthogonal to the midsagittal plane were assumed to be negligible in comparison to the geometrical changes in this plane (plane strain hypothesis).[14] Tissue quasi-incompressibility of the tongue is equivalent to area conservation and can be modeled with a Poisson's ratio value close to $0.5^{15}$. This hypothesis is well supported by 3D measurements of tongue deformation during speech production, such as the ultrasound data published by Stone et al. (1997) or the MRI data analyzed by Badin et al. (2002). It can therefore be assumed, that for better understanding of midsagittal deformations during speech production, the model is fairly accurate and can serve as a basic model to address the underlying problem and solution. It is important to analyze extreme deformation patterns occurring inside the tongue in order to understand how and why it is crucial to insert a member helically from the root of the tongue, along and near the base of the tongue into the body of the tongue.

[14] Perrier et al., 2003
[15] Zienkiewicz and Taylor, 1989

The intrinsic muscles as well as some extrinsic muscles contribute to a lesser extent to the sagittal tongue shape than the three major extrinsic muscles: the genioglossus, the styloglossus, and the hyoglossus, which are responsible for the main displacement and shaping of the overall tongue structure (Perkell, 1996). This has been reconfirmed in Perrier et al. 2003 and Buchaillard/Perrier 2009. The deformations produced by the three main muscles are by far the most extreme prototypical deformations patterns. Since deformations produced in speech are always activations of several muscles, the deformations never reach the extreme of these muscles activated solely. But if a helical pathway can fit into these extremes, deformation patterns of styloglossus, hyoglossus, posterior genioglossus and the tongue in rest position can be analyzed and with that the deformations between these extremes should be covered as well.

The problem with inserting a flexible, but in its longitudinal direction unelongatable member into the tongue in a straight or curved way is, that the length of the pathway changes with the deformations of the tongue and that change could lead to a displacement and/or will definitely cause abrasion of the member due to relative movement between member and muscle fibers. To keep the member in place, a pathway which doesn't change its length needs to be found, which will also minimize relative movement. A well-adapted helical pathway, submentally pierced near the root of the tongue, along and near the base of the tongue into the body of the tongue can fulfill that criterion. The pierced helical pathway must have nearly equal length in all the extreme deformations of the tongue.

Figure 2:
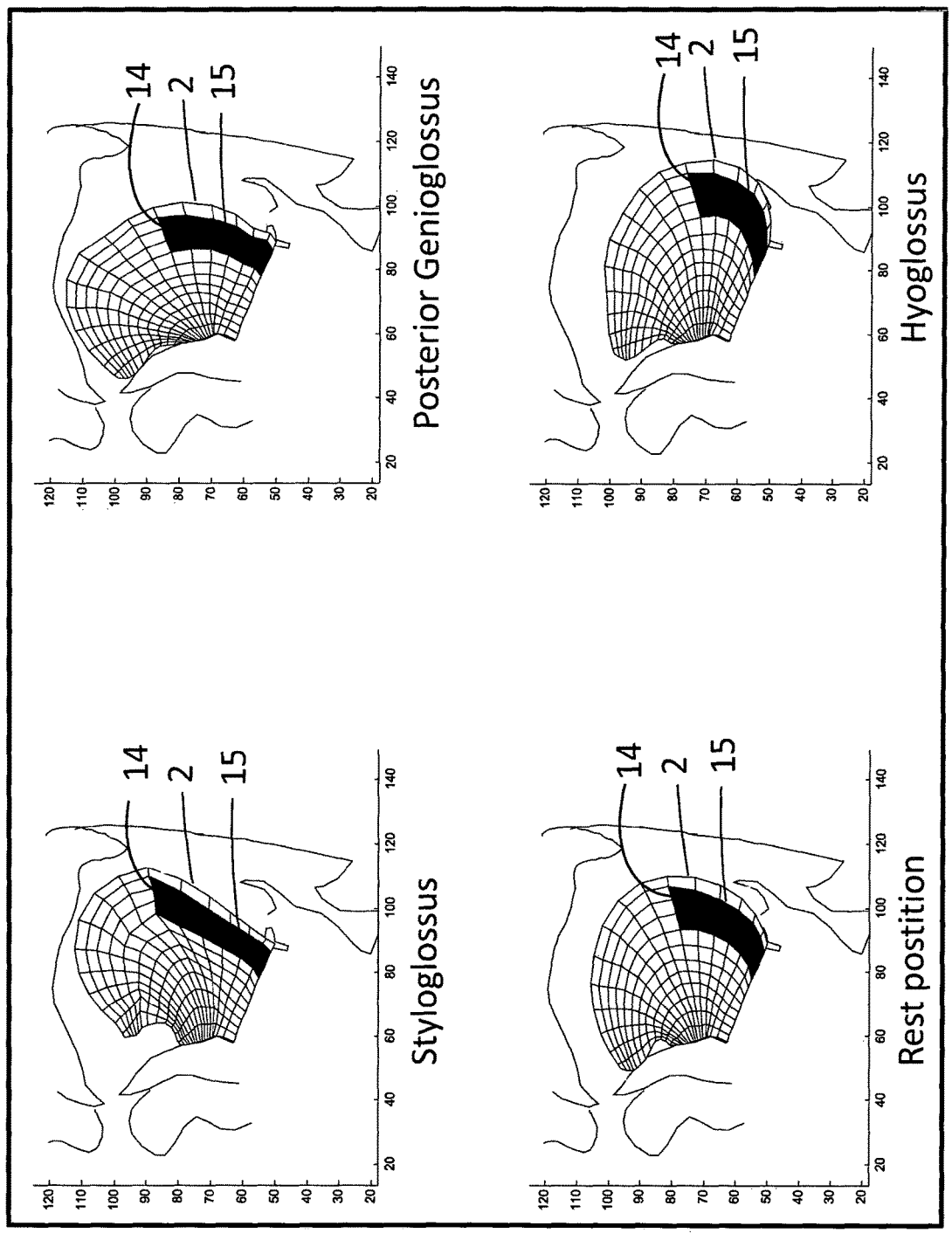
FIG. 2 is a midsagittal plane view of the pharynx of the Perrier (2003) tongue model showing preferred site of tongue implantation and associated deformations of that section induced by the three main muscles and rest position.

Now referring to FIG. 2 plots the tongue deformations induced by each modeled main extrinsic muscle with the tongue model of Perrier (2003). Direction and amplitude of the simulated deformations were verified to be compatible with data measured (Badin et al., 1995) The tongue shapes 2 shown in the figure are similar to those seen in a number of cineradiographic studies of speech movements (e.g., Perkell, 1969, Bothorel et al., 1986, Napadov, 1999 and 2002). The darkened section changes in length 13, width 14 and curvature as muscle are being activated. Piercing an helical pathway into that section and putting an implant inside that pierced pathway can also change length and width, because it can substitute an increase in pitch with a decrease in diameter and vice versa. If the right pathway and helical properties are adequately defined, it could therefore deform and behave like the tongue.

Figure 3:
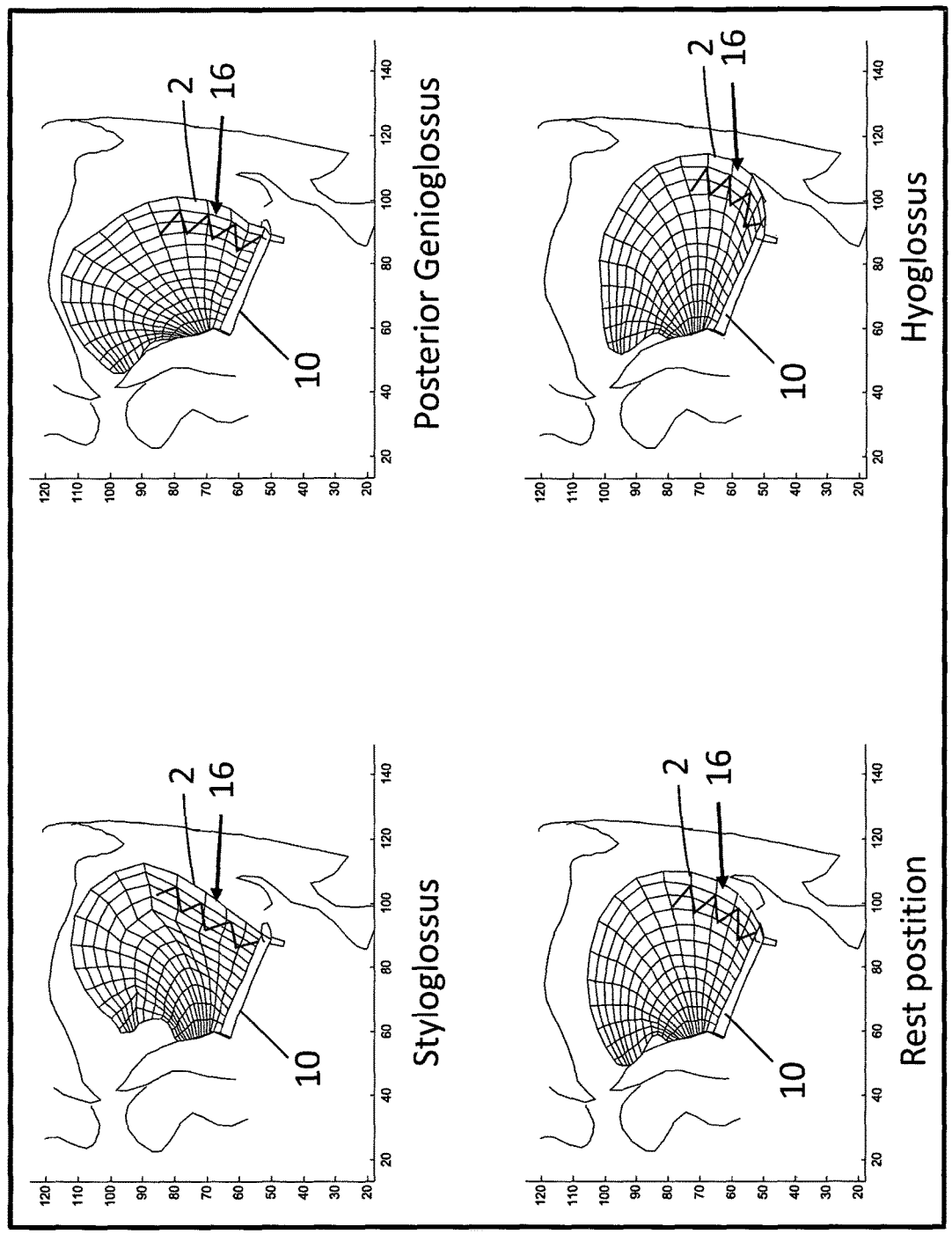
FIG. 3 is a midsagittal plane view of the pharynx of the Perrier (2003) tongue model showing a helical pathway and associated deformations of that section induced by the three main muscles and the rest position.

To achieve that, submental helical piercing is performed with the tongue in deformed state, like the deformation produced by styloglossus activation. As explained in International Patent Application PCT/IB2011/002878 entitled Helical Inserter, a tool formed like spatula is put into the oral cavity down the pharynx to level of the epiglottis and the tongue is being pulled anteriorly with that spatula (not shown in drawings), such that the base of the tongue is being straightened before piercing the tongue helically. Such a pathway for the helical section 16 is shown in FIG. 3 for the deformation induced by the three main extrinsic muscles and the rest position. For simplicity of measuring length, a zigzag line is chosen to represent the helix, as it is a reasonable approximation in 2D.

Figure 4:
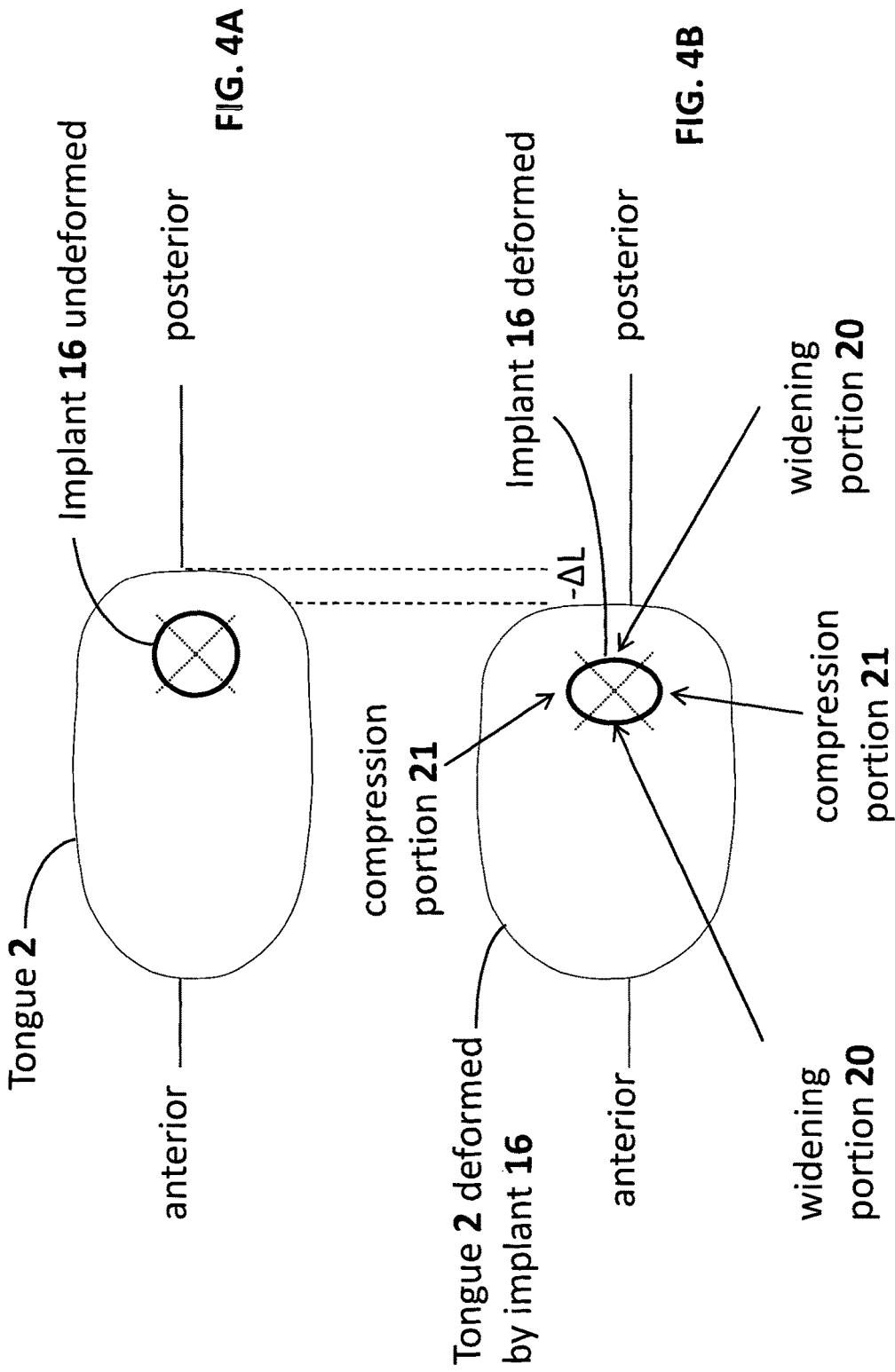
FIG. 4A is a top view on the tongue showing the different deforming portions of a helical implant inside the tongue in undeformed state.
FIG. 4B is a top view on the tongue showing the different deforming portions of a helical implant inside the tongue in deformed state.

Now referring to FIG. 4, the helical section inside the body of the tongue 2 has four different portions: a widening portion 20 anteriorly and posteriorly and two compressing portions 21, which deform the tongue in a protruding way.

Figure 5:
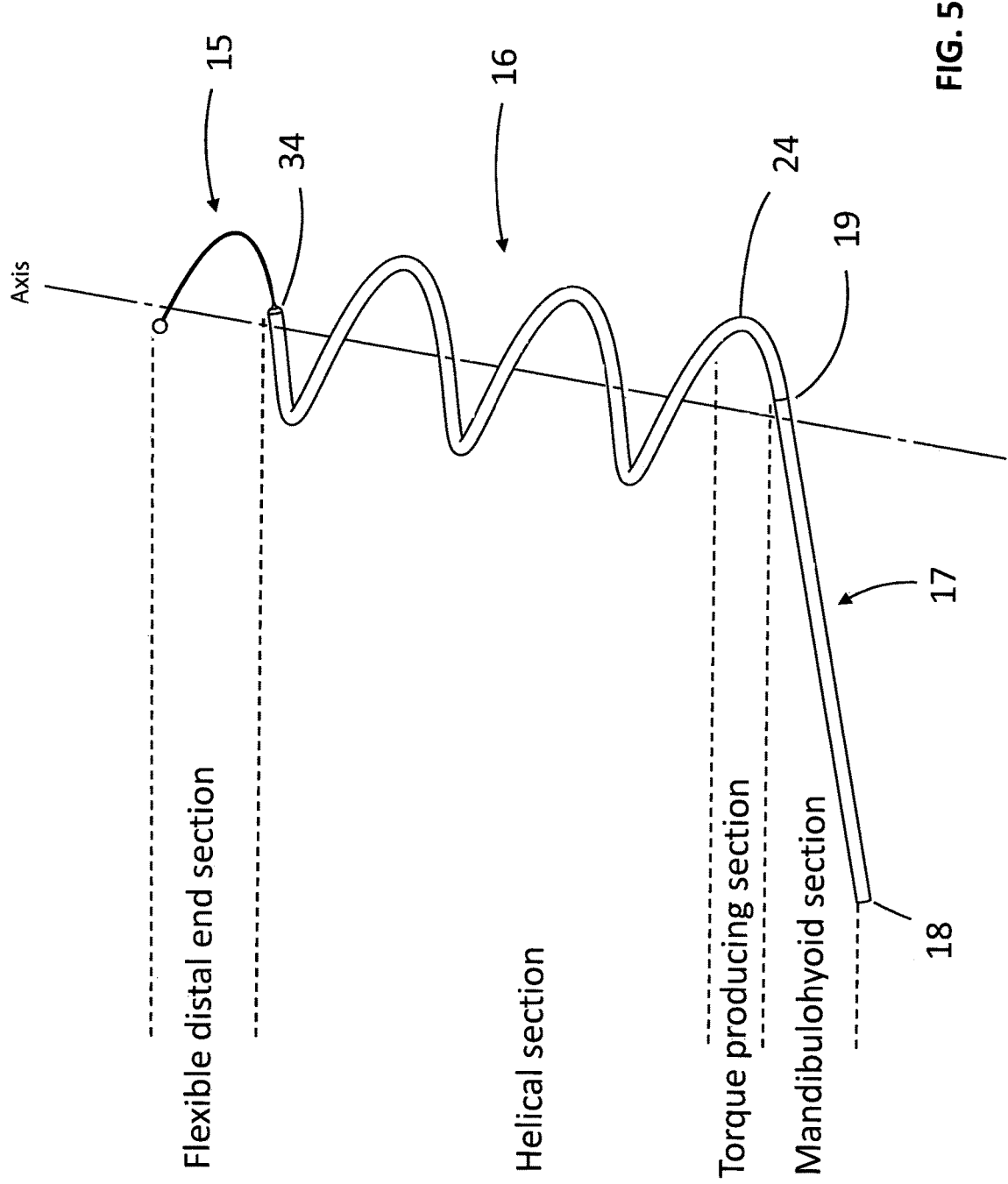
FIG. 5 is a front view of a tongue implant showing all sections.
Figure 6:
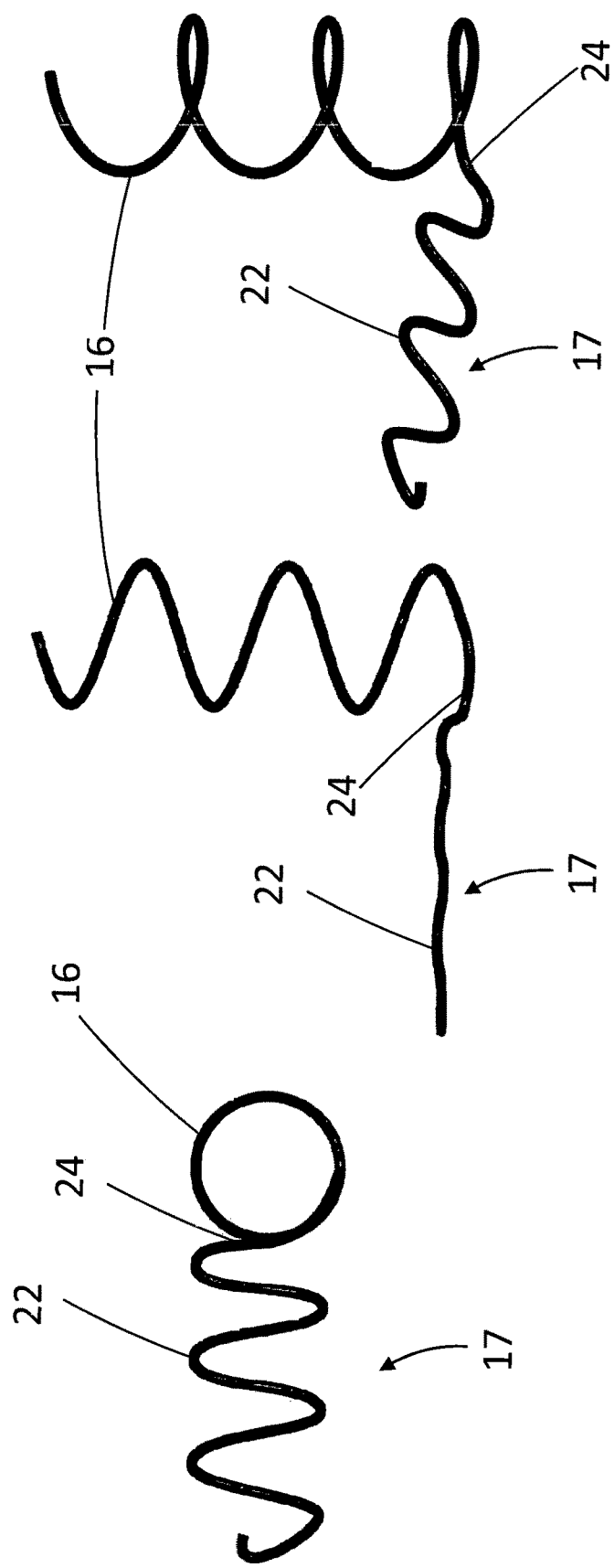
FIG. 6A shows a bottom view of the implant with the mandibulohyoid section for force distribution shaped in serpentine way without the flexible distal end section.
FIG. 6B shows a side view of the implant with the mandibulohyoid section for force distribution shaped in serpentine way without the flexible distal end section.
FIG. 6C shows an iso view of the implant with the mandibulohyoid section for force distribution shaped in serpentine way without the flexible distal end section.

Now referring to FIG. 5. explaining the basic setup for all embodiments comprising four sections: the flexible distal end section 15, the helical section 16 inside the body of the tongue 2, the torque providing section 24 at entry of the root of tongue, and the mandibulohyoid section 17 for force distribution. The flexible distal end section 15 provides means for stabilization of the member distally inside the body of the tongue allowing small displacement of the helical section 16 as the tongue is performing its physiological tasks. The helical section 16 providing means to change state: in first state (inactive) it can deform likewise the tongue needing minimal deformation forces, in second state (activated) exerting a force on the tongue essentially stiffening it along the base of the tongue and protruding the tongue. The mandibulohyoid section providing means for attaching it to the mandible bone 12 proximally, then positioned in between the paired geniohyoid 10 and root of the tongue to be affixed to the hyoid bone 19 distally, when changing its state, pulling the hyoid bone forward and with that the whole body of the tongue, deforming preferably to a helical form or a serpentine shape to shortening that section. In another embodiment 1''', the device could also be permanently in second state. Affixing mandibulohyoid section 17 to the mandible bone 12 an option, as it may not be necessary for some patients, as well as the torque producing section 24 may not be affixed it to the hyoid bone 4. Now referring to FIG. 6, in another embodiment, the mandibulohyoid section 17 is neither attached to hyoid bone 4 nor to the mandible bone 12. There is provided a force distribution section placed between geniohyoid 10 and root of tongue having a shape of a serpentine line 22 to distribute the force produced by the torque section 24 and compress the body of the tongue stiffening and protruding it.

Figure 7:
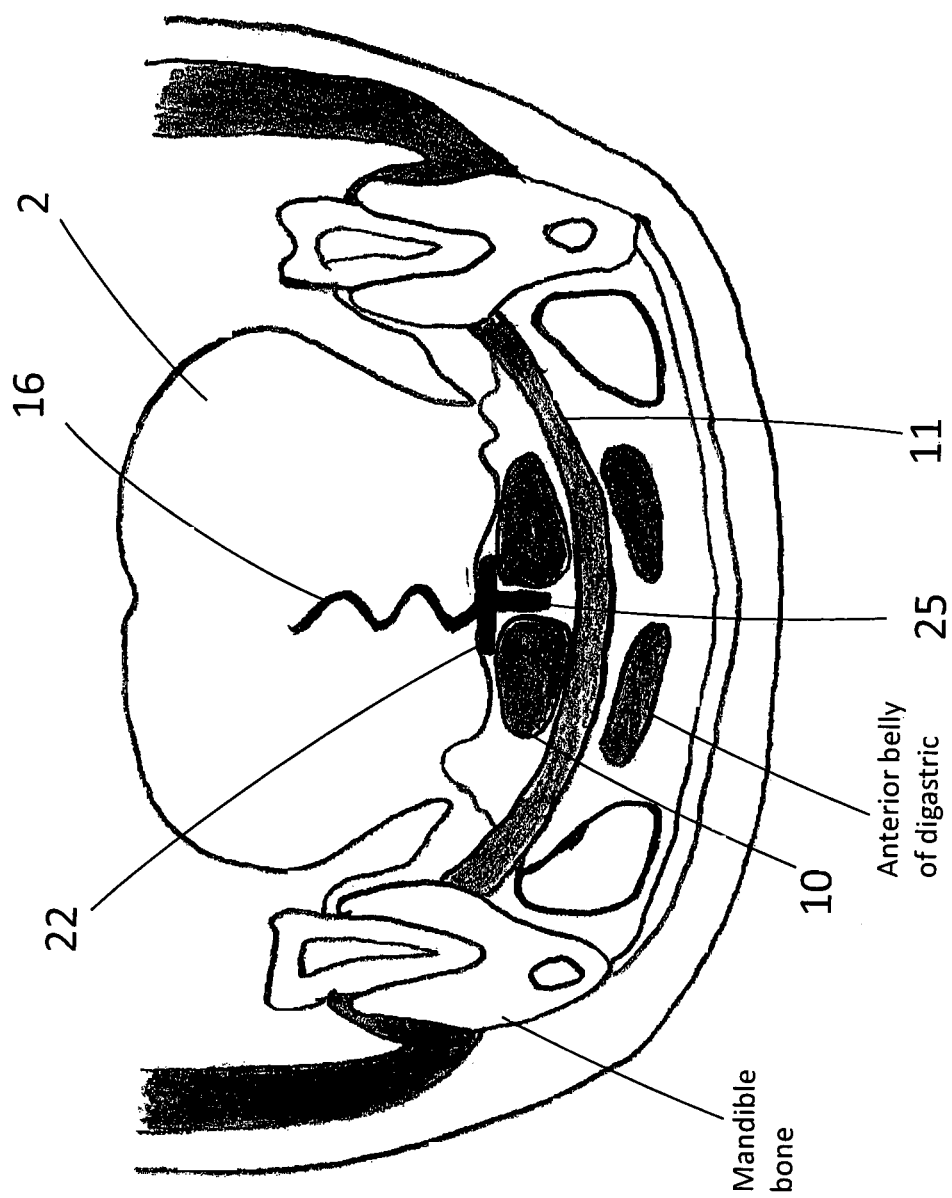
FIG. 7 is a coronal plane cross section of the mandible showing placement of the mandibulohyoid section including a fin.

Now referring to FIG. 7, to prevent dislocation laterally of the mandibulohyoid section, a fin 25 can be shaped for placement without attachment between the two geniohyoid muscles 10.

Figure 25:
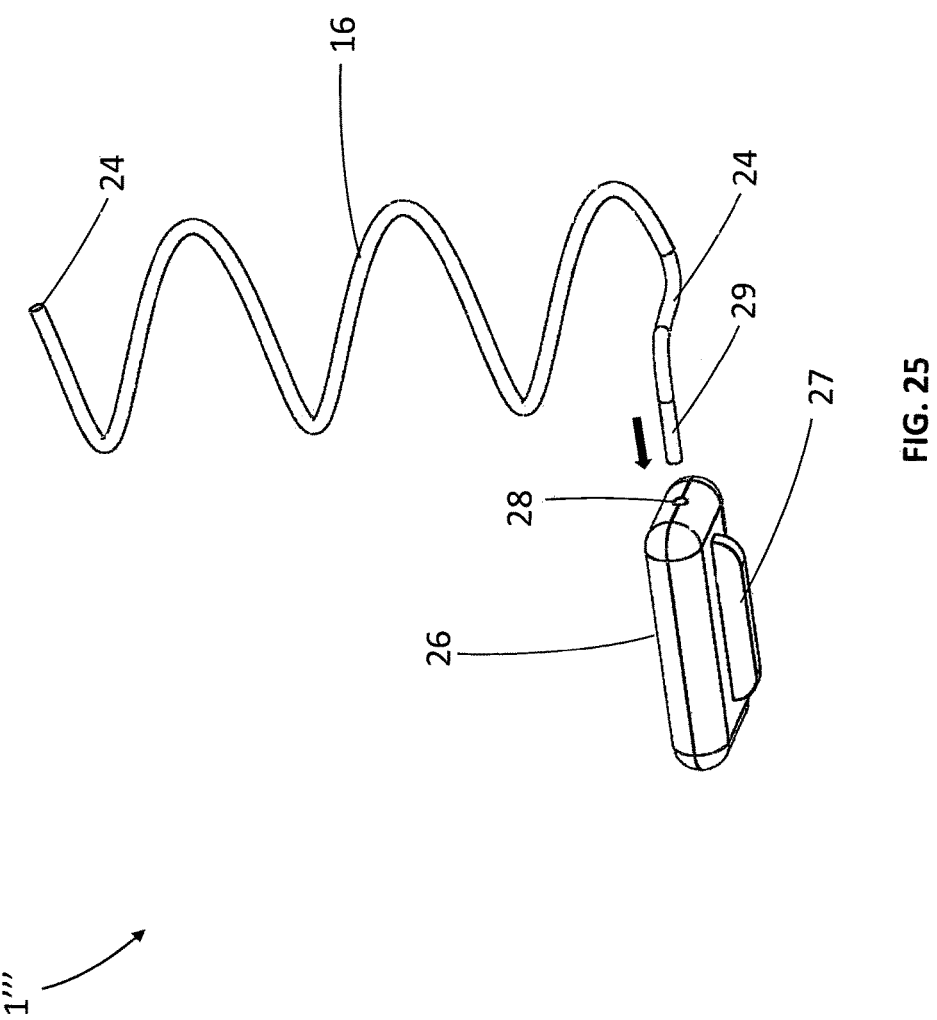
FIG. 25 is another embodiment for a force distributing mandibulohyoid section.

Now referring to FIG. 25, explaining another embodiment of the mandibulohyoid section in a passive device 1''', instead of creating a shape like a serpentine line for force distribution of the torque producing section 24, a force distributing part 26 could be placed between geniohyoid 10 and body of tongue or between mylohyoid 11 and geniohyoid 10, preferably made of a polymer. This part would be slipped into the target site and then attached to the member as indicated by the arrow, for example by an aperture 28 with a corresponding distal end 29 of the member. Again, to prevent dislocation laterally, a fin 27 is added to be placed between the two geniohyoid muscles 10.

Figure 8:
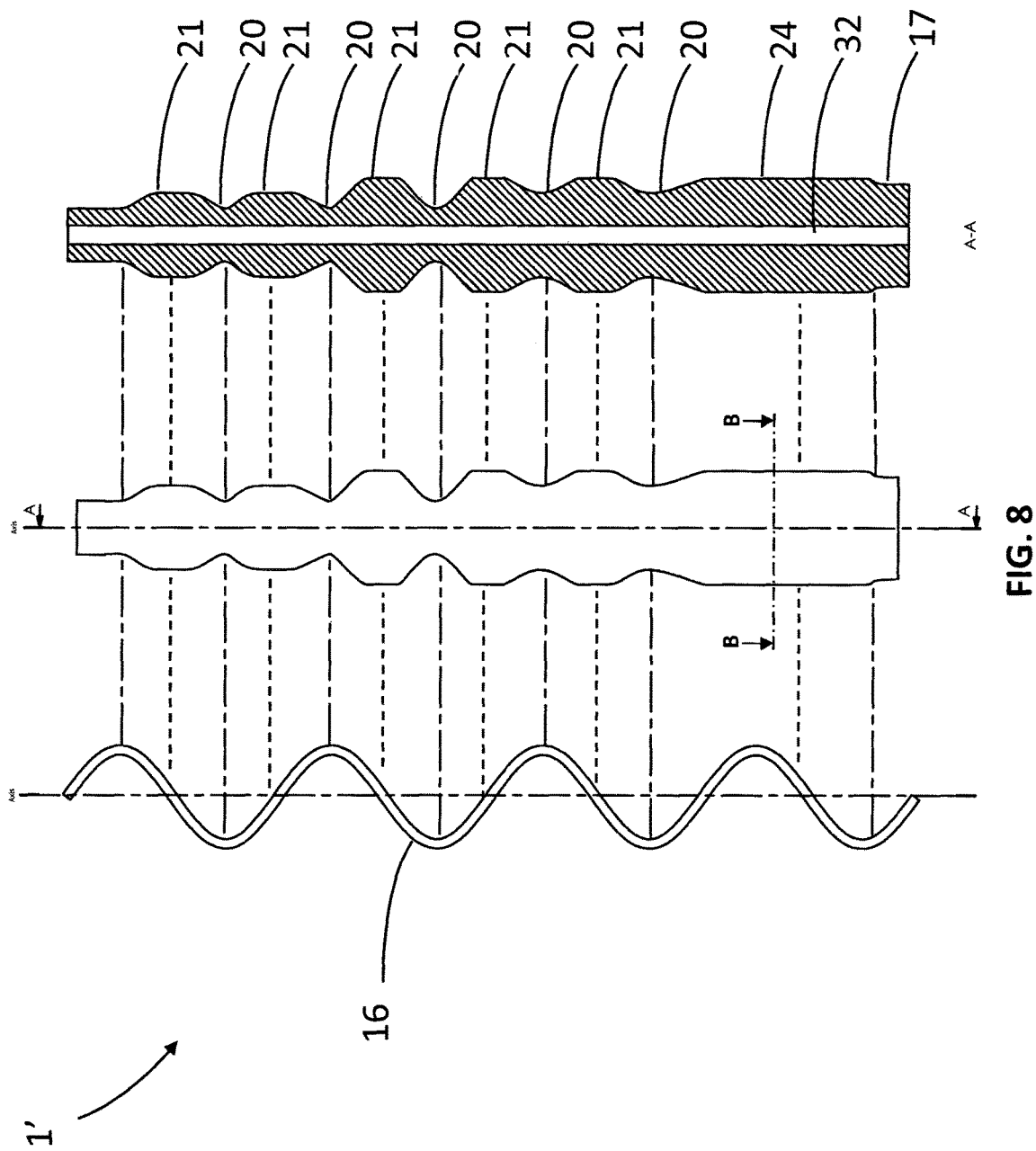
FIG. 8 is a helical section of the first embodiment with an exaggerated schematic view of SMA actuator Showing a profile distribution of the helical section and cross section A-A as indicated.
Figures 10A, 10B, 10C:
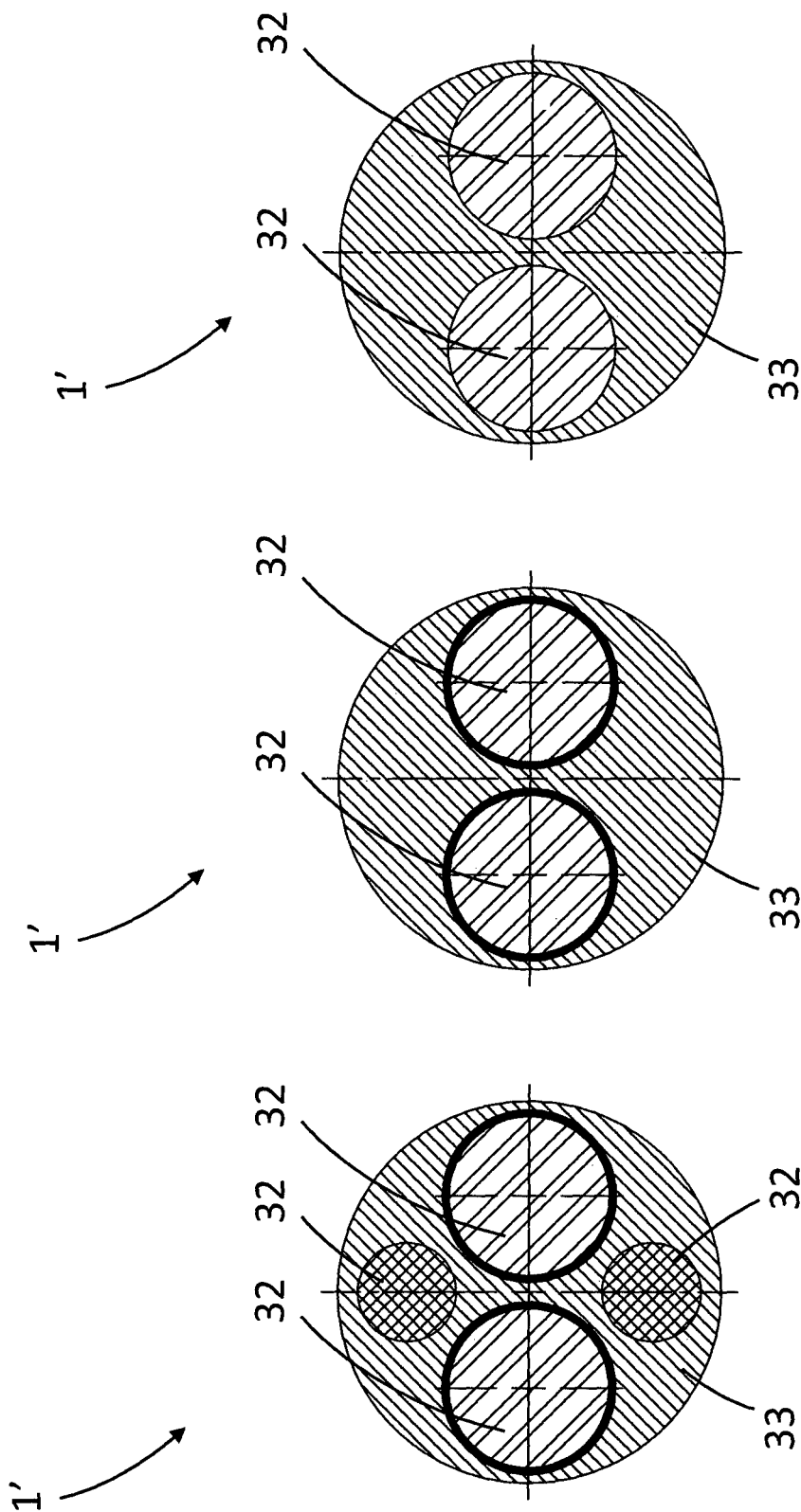
FIGS. 10A-10C show different cross sections of the inside of a mandibulohyoid section having a plurality of leads without the SMA actuator tube around of it
Figures 11A, 11B:
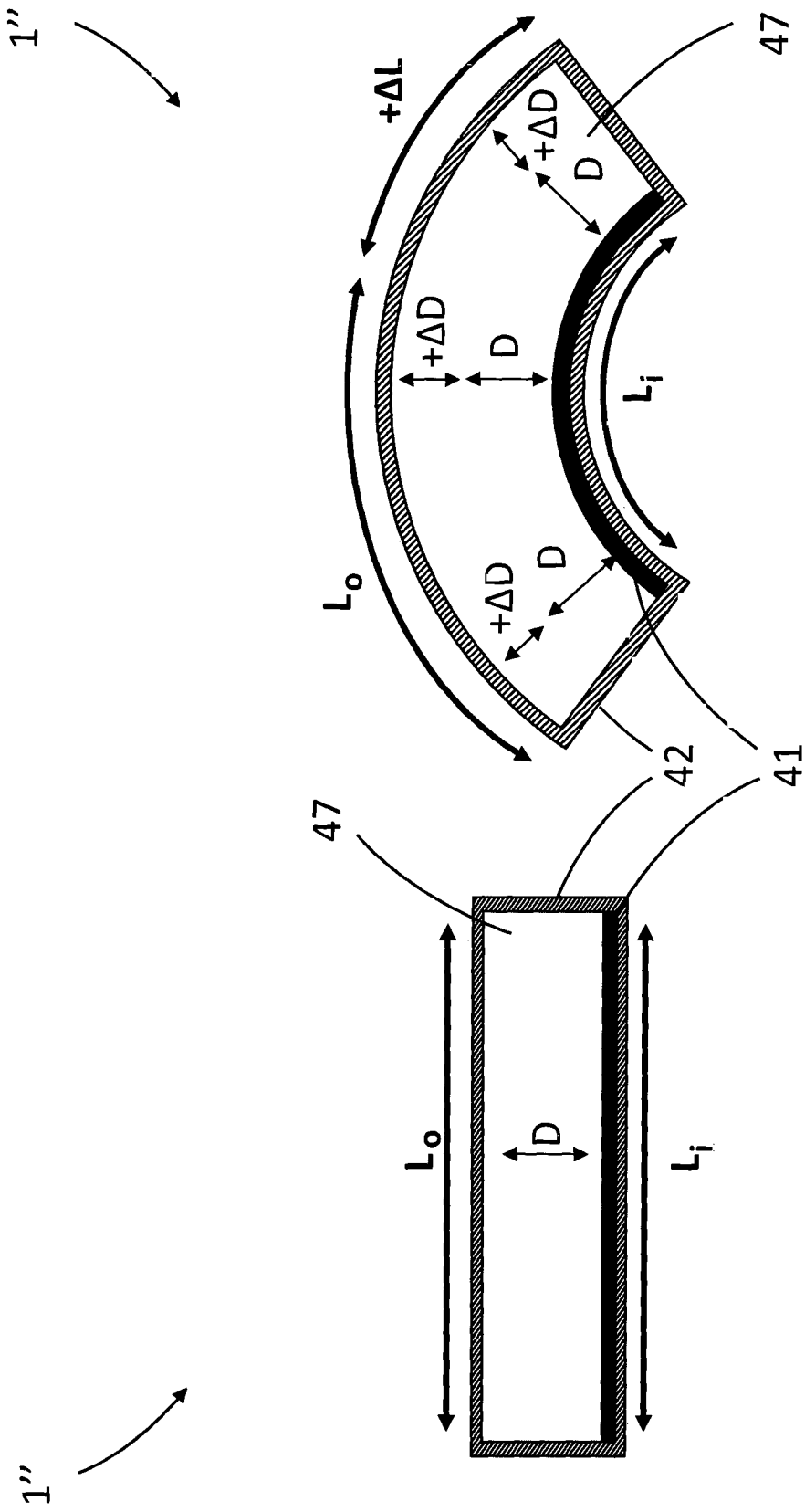
FIG. 11A is a schematic longitudinal cross section of the helical section of the fluid actuator in unpressurized state
FIG. 11B is a schematic longitudinal cross section of the helical section of the fluid actuator in pressurized state showing bending
Figure 12C:
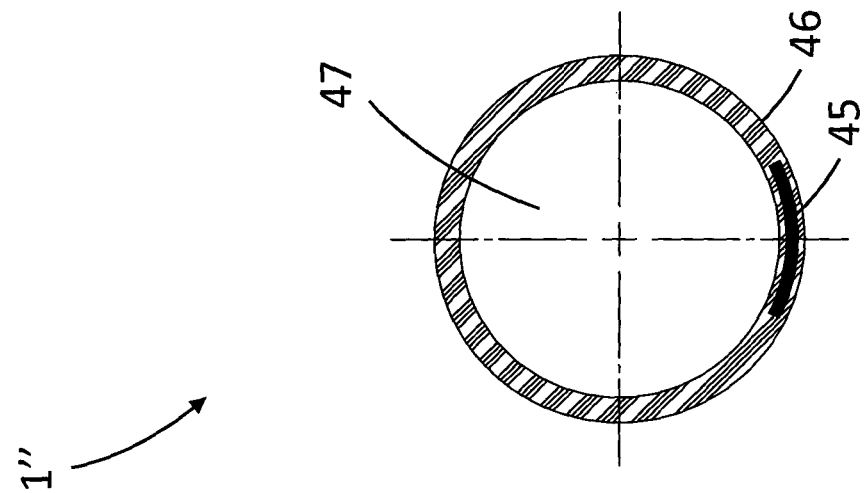
FIG. 12C shows a transverse cross sections of the helical section of the fluid actuator having an unelongatable belt
Figure 12B:
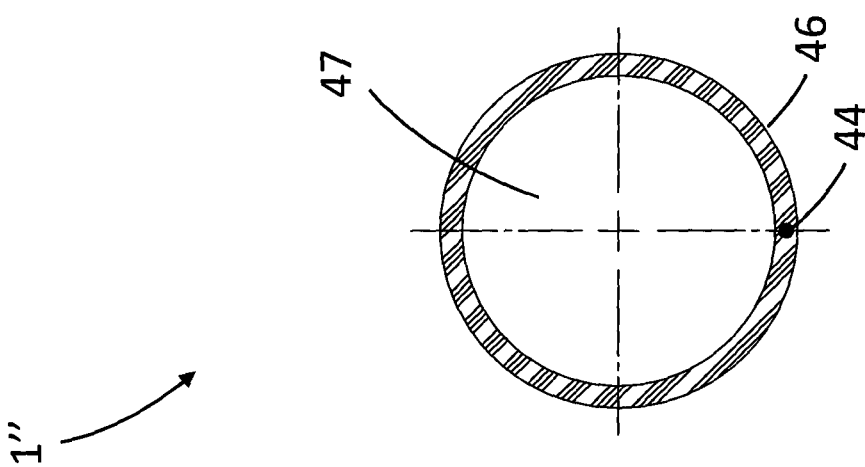
FIG. 12B shows a transverse cross sections of the helical section of the fluid actuator having an unelongatable fiber
Figure 12A:
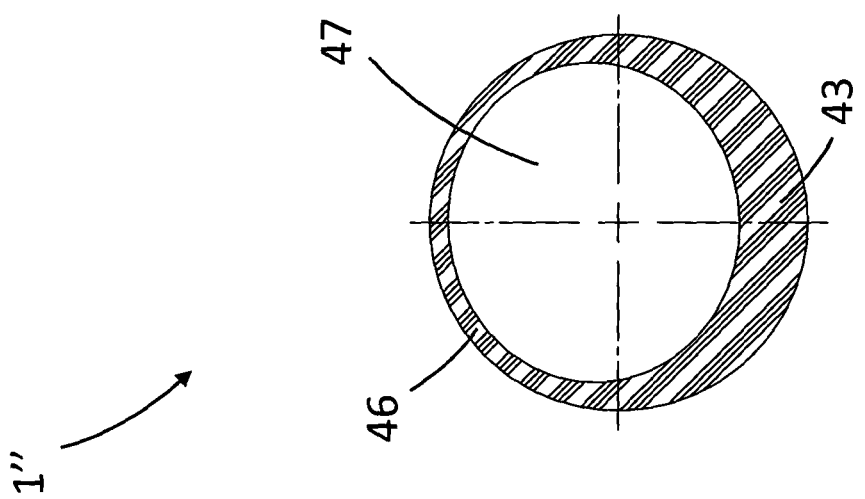
FIG. 12A shows a transverse cross sections of the helical section of the fluid actuator having a decentered inner lumen
Figures 14A, 14B:
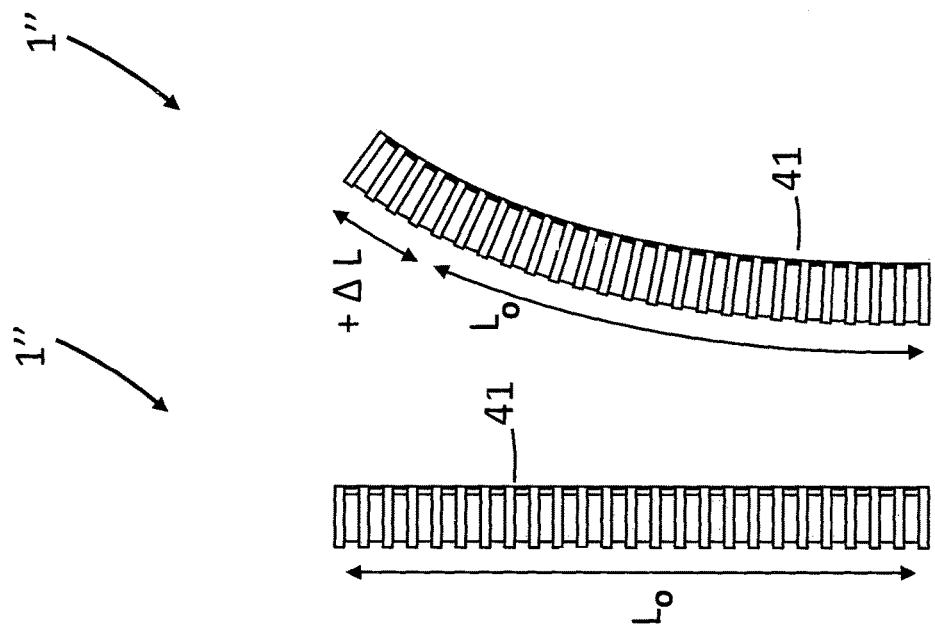
FIG. 14A is a partial front view of a fluid actuator in unpressurized state
FIG. 14B is a partial front view of a fluid actuator in pressurized state showing bending
Figure 13:
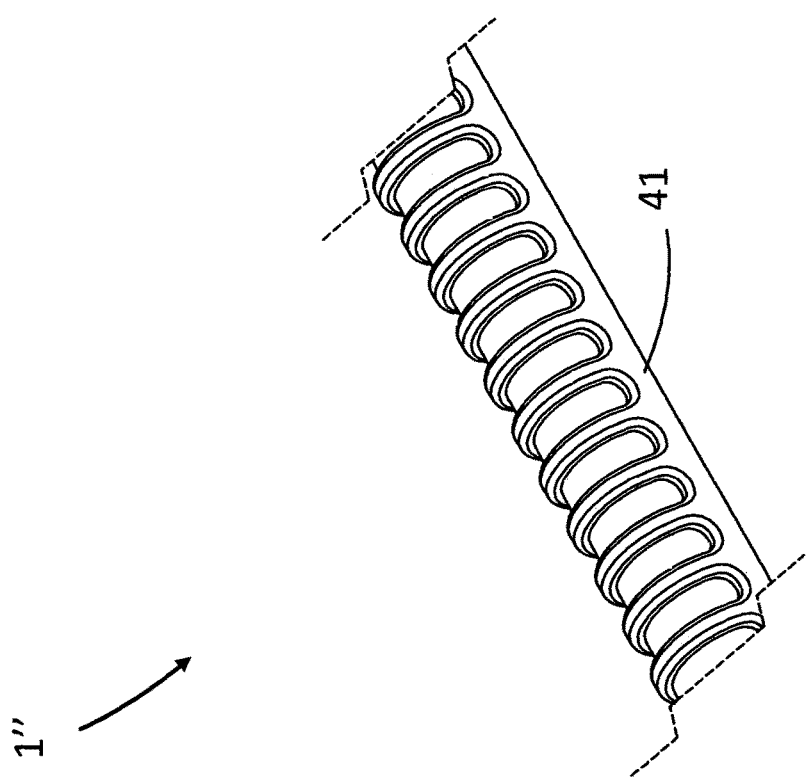
FIG. 13 is a perspective, partial view of a different helical section of the fluid actuator

Now referring to FIG. 8, explaining the helical section 16 of the first embodiment 1', a tongue actuator, which is made of a shape memory alloy, which is preferably Nitinol.

Shape memory alloys (SMA), because of their unique mechanical characteristics and shape memory effect (SME), have been widely used as force and displacement actuators in many fields.[16] Nickel-Titanium (Nitinol or NiTi) Superelastic and Shape Memory Alloys has become the material of choice for self-expanding, stents, stent grafts, filter, baskets and other devices for interventional procedures. With the demand for high precision NiTi material in different forms, especially wire and tubes, immense progress has been made in the manufacturing processes, making it possible to get material in a wide range of geometries and sizes.

[16] Duenng et al, 1990

What makes Nitinol unique is its ability to exist in two different temperature-dependent crystal structures (phases) called martensite (lower temperature) and austenite (higher temperature). The solid phase change in Nitinol, known as the reversible martensitic transformation, can be induced by temperature. When martensite NiTi is heated, it begins to change into austenite. Several properties of austenite NiTi and martensite NiTi are notably different. When the material is in its martensite form, it is soft and ductile and can be easily deformed (Deformation pressure is 10,000 to 20,000 psi). When heated to its higher temperature form (austenite), it will recover its original shape and rigidity. The yield strength with which the material tries to return to its original shape is considerable: 35,000 to 70,000 psi. This is called the one-way shape memory effect. Upon cooling, the martensite will reform and the shape retained.

The temperature at which this phenomenon starts is called austenite start temperature ($A_s$). The temperature at which this phenomenon is complete is called austenite finish temperature ($A_f$). When austenite NiTi is cooled, it begins to change into martensite. The temperature at which this phenomenon starts is called martensite start temperature ($M_s$). The temperature at which martensite is again completely reverted is called martensite finish temperature ($M_f$)[17]

[17] BUEHLER et al., 1967

Very importantly, one should be aware that there is a thermal hysteresis or difference between the forward and reverse transformation paths. The temperature range for the martensite-to-austenite transformation that takes place upon heating is somewhat higher than that for the reverse transformation upon cooling (Fig. A). The difference between the transition temperatures upon heating and cooling is called hysteresis. Hysteresis is generally defined as the difference between the temperatures at which the material is in 50% transformed to austenite upon heating and in 50% transformed to martensite upon cooling. The composition and metallurgical treatments have dramatic impacts on transition temperatures and hysteresis; today, transition hysteresis as low as 10° C. or even lower is achievable.

In one embodiment the member should be fully in martensite state at body temperature, which means reversing from the austenite state, the member needs to cool down below the martensite finish temperature $M_f$, which is lower than austenite start temperature $A_s$.

While most metals can be deformed by slip or dislocation, NiTi responds to stress by simply changing the orientation of its crystal structure through the movement of twin boundaries. A NiTi specimen will deform until it consists only of the correspondence variant, which produces maximum strain. However, deformation beyond this will result in classical plastic deformation by slip, which is irrecoverable and therefore has no 'memory effect'. If the deformation is halted midway, the specimen will contain several different correspondence variants. If such a specimen is heated above Af, a parent phase with an orientation identical to that existing prior to the deformation is created from the correspondence variants in accordance with the lattice correspondences between the original parent phase and each variant.

The austenite crystal structure is a simple cubic structure, while martensite has a more complex rhombic structure. This phenomenon causes the specimen to revert completely to the shape had before the deformation.[18] The above phenomenon is the basis of such special properties as the shape memory effect and superelasticity.

[18] GIL et al., 1998

NiTi senses a change in ambient temperature and is able to convert its shape to a preprogrammed structure. The properties of Nitinol rely on its dynamic crystalline structure. The molecular structure is sensitive to external stress and temperature. The alloy has three defined temperature phases.

1. Austenite Phase. Temperature is above transition temperature. The transition temperature varies depending upon the exact composition of the Nitinol alloy; today it can be fine-tuned to a specific temperature. The yield strength with which the material tries to return to its original shape is considerable; 35,000 to 70,000 psi. The Crystalline structure is cubic.

2. Martensitic Phase. Low temperature phase. The crystal structure is needle-like and collected in small domains. Within the small domains the needle-like crystals are aligned. The alloy may be bent or formed easily. Deformation pressure is 10,000 to 20,000 psi. Bending transforms the crystalline structure of the alloy producing an internal stress.

3. Annealing Phase. High temperature phase. The alloy will reorient its (cubic) crystalline structure to "remember" its present shape. The annealing phase for the Nitinol wire is about 540° C. A CNC torsion spring coiler machine like the FMU series of German producer Wafios could be used to produce a tube, for example a stainless steel tube, having the desired shape for the second state. The Nitinol tube or wire will be pulled into the deformed tube for annealing.

The mechanical properties of NiTi depend on its phase state at a certain temperature.[19] Generally, there are two basic mechanical demands for the material and design of the tongue actuator. It should be flexible during the day and at night prevent or recover apneic events by stiffening the tongue and pressing or pushing it forward. Service stresses must be safely below the yield strength of the material, and in cyclic loads the service stress must be kept below the fatigue limit. This can be influenced by well choosing the helical path the member runs through as well as the deformation occurring by switching to austenite state. Both influence the deformations of the member and with it strain to the material. Since strain is of major influence to martensitic transformation cycles, it is advised to keep strain low, at best below 2%. The common mechanical properties of martensitic and austenitic NiTi are presented in Table 1.

[19] BUEHLER et al., 1967

The low elastic modulus of NiTi and its unique high fatigue properties, which are also related to its martensitic transformation, are of benefit for this specific application. In martensite the member can be easily deformed by the tongue, which happens all the time during speaking. A solid member of most other alloys couldn't handle such a cyclic load behavior, but Nitinol can due to its atomic structure.

TABLE 1

| Selected mechanical properties of NiTi | Austenite | Martensite |
| --- | --- | --- |
| Ultimate tensile strength (MPa) | 800-1500 | 103-1100 |
| Tensile yield strength(MPa) | 100-800 | 50-300 |
| Modulus of elasticity (GPa) | 70-110 | 21-69 |
| Elongation at failure (%) | 1-20 | Up to 60 |

It is feasible to vary the critical transition temperatures either by small variations of the Ti/Ni composition or by substituting metallic cobalt for nickel. While laser welding can be applied for joining NiTi alloys, joining of NiTi to other materials is still a problem. The number of materials that can be laser welded to NiTi is very limited. Among those are tantalum, copper and platinum.

Again referring to FIG. 8, a tube having a constant diameter could be used, but this would create too much rigidity towards the distal end inside the tongue body. Another basic shape would be cone like because the most force for deformation of the tongue in second state is need at the root of the tongue and less force is required towards the flexible distal end of the member inside the tongue body. However, since it isn't necessary to have the same amount of force exerted along the whole length of the member, the tube can be grinded, laser cut or structured laser ablated to a profile such that with every half turn it is thinner (the widening portion 20) than the compressing portion 21 in between. The smaller profile 20 is used in first inactive martensite state at body temperature that the tongue can deform at these sections, the member only requiring minimal deformation forces, when the tongue is performing its physiological tasks during daytime. The thicker sections are needed in second austenite state to deform the tongue at night when OSA occurs. Since the force that the member can exert on the tongue is directly depended on square area, this is the section deforming and changing the stiffness of the tongue. The compression portion of the helix facing posteriorly (towards the pharynx) must be stronger than the ones facing anteriorly (towards the front teeth). This creates segments between each pitch and deforms the tongue in a protruding way. Forces exerted should be between 2 kPa and 25 kPa. In an active device, the actuator is electrically heated by connecting it to an implanted device having an accumulator delivering electric pulse modulation as OSA occurs. Since the thinnest sections heat up the fastest, copper, gold or silver could be vaporized onto that section serving as a bridge for the electrons. Another possibility would be to better thermal shield these sections.

Desired Nitinol Properties:

Martensite: low deformation pressure, about 10'000 psi

Martensitic transformation: high yield strength, about 70'000 psi Transition temperature: martensite at body temp, As at about 39° C.

Transition hysteresis: low, today Δ10° C. or lower is possible

Cycle times: high, by keeping strain as low as possible (below 2%). Since there is no pulling force in longitudinal direction, hence there is no elongation of the member, only leaving deformations, making it possible to have more than 100 million martensitic transformations.

Transition duration: very fast, few milliseconds are possible, but not needed. High yield strength for the martensitic transformation is more important.

Diameter: between 10 μm and 250 μm for a wire or a tube

Now referring to FIG. 9A-9C, showing different cross sections B-B as indicated in FIG. 8, the helical section 16 could be of round or oval shape. The hull 30 of the Nitinol tube 31 is coated preferably with a fluoropolymer for thermal insulation and electrical isolation, but silicon rubber or the like could be used as well. Fluoropolymers are widely used in medical implants like electric leads in cardiac pacemaking because of their biocompatibility, corrosion stability and low friction values. The coating must be thick enough as to not burn the muscle fibers in contact with the heated member (keeping surface temperature of the implant below of about 45° C.), which is in a range of 100-200 μm, but due to loss through abrasion over time, the thickness is increased up to 400 μm, giving an overall diameter of about 1 mm. The lead 32 inside the tube 31 is also made of Nitinol, since even a multifilar wire of another material may not handle the ongoing stress produced by deformations of the tongue leading to material fatigue. The inner Nitinol is coated for electric insulation with a silicon rubber 33 or the like having elastic properties, since the neutral plane always changes depending on the deformation of the whole implant, as the tongue performs its physiological tasks. Coating the inner lead with an inelastic material would lead to slip and with that create abrasion inside the tube. In assembly, the NiTi tube could be pressed open by using compressed air or with a fluid, such that the inner lead, coated after heat treatment, can be pulled inside. When heated up above transition temperature, the shape memory effect makes the tube and the lead formfitting. The distal end of the helical tube 31 and the lead 32 inside must be joined together to close the electric circuit by means of laser welding. The polymeric flexible distal end 34 of the member is joined with the fluoropolymer coating of the tube by means of laser welding.

Figure 24:
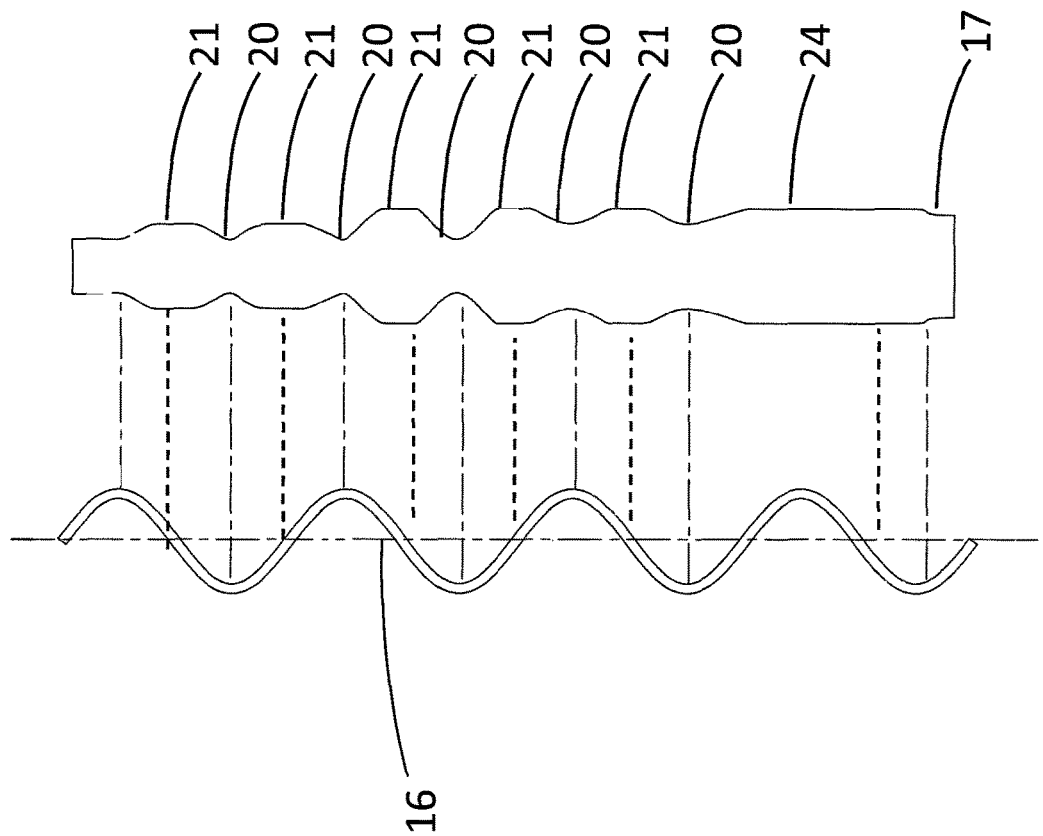
FIG. 24 is a helical section of the third embodiment with an exaggerated schematic view of SMA implant showing a profile distribution of a helical section

Now referring to FIG. 24. in another embodiment 1'", the passive tongue deformation implant, the implanted member is permanently in austenite state at body temperature, thus making an energy source and leads inside the member to induce electrical heating obsolete. However, a passive device will create additional rigidity to the tongue. In this case the member is only one solid NiTi wire having a protective coating, preferably a fluoropolymer like ETFE or FEP as well, because of the low friction values and biocompatibility. The wall thickness of the coating should also be about 400 μm. Forces exerted should be between 2 kPa and 25 kPa, by grinding the widening portion 20 anteriorly and posteriorly thinner than the compressing portion 21 in between.

Now referring to FIGS. 11-20, explaining the second embodiment 1", which is a fluid filled tongue actuator 40. Overall diameter of the tube is preferably below 2 mm. In its first inactive state the tube 46, made of a biocompatible fluoropolymer, preferably an FEP, is unpressurized and therefore requiring minimal deformation forces, when the tongue is performing its physiological task during daytime. In its second active pressurized state, the helical section 16 deforms to a preferred curved shape making it rigid exerting a deformation force onto the tongue. According to Pascal's Principle, the pressure is transmitted undiminished in an enclosed static fluid. The inner side of the helical section facing toward the axis must keep is length 41 whilst the outer side can change its diameter+ΔD 42 and expand leading to an increase in length+ΔL and curving or bending of the member, essentially deforming, stiffening and changing the rigidity of that section. As can be seen in FIG. 12A, this could be achieved by increasing wall thickness 43 at the inner side of the helix towards the axis by decentering the inner fluid filled lumen 47 of the tube, the opposite wall 46 having a smaller wall thickness. Another option as shown in FIGS. 12B and C, would be integrating a second unelongatable cable/fiber 44 or belt 45, for example made of polyamide PA at the inner side of the helical section facing toward the axis. Ribs can further enhance deformation forces, as only the intercostal section can expand. To increase flexibility during daytime, the fiber 44, belt 45 or thickened section 43 may be broken up at certain sections 57.

The tube is at best filled with a physiological saline fluid solution 47, because in case of fissure due to material failure, a saline fluid can't harm to the human body. However, due to the fact that the fluid is pressurized at night, some water molecules are pressed out through the hull of the member (reverse osmosis), since polymers are slightly permeable. To avoid fluid loss over time, the saline concentration inside the tube must have a higher solute concentration than the human body (NaCl 0.9%) leading to an osmotic pressure differential, in order to equalize the solute concentrations on the two sides during unpressurized daytime and refill the tube with water molecules. An advantage of FEP is its very low permeability minimizing fluid loss. The fluid actuator will be connected to an implantable pressurizing device, which will be activated at the onset of sleep.

The mandibulohyoid section 17 should shorten as it is pressurized, as can be seen in FIG. 17-20. This can be achieved by either leaving out thickened 43 sections, fiber 44 or belt 45. Another possibility would be to introduce ribs 48 all around, which can't expand like the intercostal sections 49 in between, or by just increasing overall diameter 50+ΔD. Another option is producing it in an accordion bellows 58 like design, as shown in FIG. 17.

Figure 23:
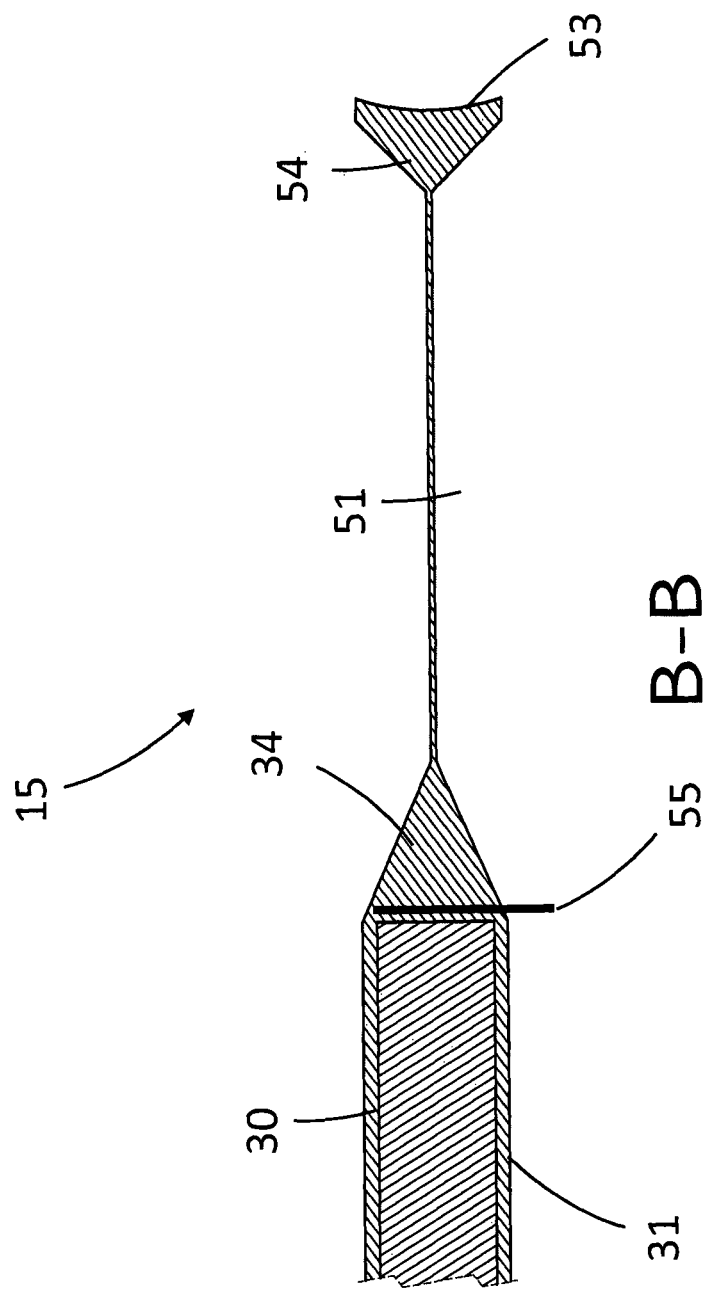
FIG. 23 shows a longitudinal cross section of a different flexible distal end

Now referring to FIG. 21-23, explaining the flexible distal end section 15 of all actuator embodiments 1', 1" and as well as the passive implant embodiment 1''', the flexible distal end must be designed that the member is neither displaced nor that it can poke tongue tissue. But it must leave the option of extraction of the implant without cutting the whole tongue open, but rather just by pulling it out of the body of the tongue. A polymeric fiber 51, for example a polyamide, substantially smaller in diameter, for example 30 μm, is attached at the flexible distal end 34 of the helical section 16. At the distal end 52 of the distal end section 15, a sphere could be attached to the fiber 51 having the same diameter as the helical section 16, but it could have other shapes. The pressure inside the tongue tissue 56 will hold in place. Another option as shown in FIG. 23 would be to shape the distal end 34 of the helical section 16 like a cone and to shape the distal end of 15 like a cone 54 as well, but facing reverse direction. This allows for small displacement, but the cone shape will make it slide back to initial position. This could be further enhanced by shaping the distal end of the distal end section 53 in concave form. The distal end section and the helical section can be joined together for example by means of laser welding 55 or pressfitting it with the tube.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

The copyrights are owned by the Applicant(s) or their assignee and, with respect to express Licensees of the rights defined in one or more claims herein, no implied license is granted herein to use the invention as defined in the remaining claims. Further, vis-à-vis third parties, including the public, no express or implied license is granted to reproduce, prepare derivative works, distribute copies, display, or otherwise use this patent specification, inclusive of the appendix hereto and any computer program comprised therein, except as an appendix to a patent issuing hereon.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the claims which ultimately issue in this application.

ADDENDUM

The following articles or documents are incorporated herein by reference thereto and relied upon: International Patent Application PCT/IB2011/002878 entitled: Helical inserter U.S. Patent Documents U.S. Pat. No. 7,909,037 dated Mar. 22, 2011, TETHERED AIRWAY IMPLANTS AND METHODS OF USING THE SAME
U.S. Pat. No. 7,909,038 dated Mar. 22, 2011, TONGUE STABILIZATION DEVICE AND METHOD OF USING THE SAME
U.S. Pat. No. 7,401,611, dated Jul. 22, 2008, AIRWAY IMPLANT
U.S. Pat. No. 8,327,854 dated Dec. 11, 2012, PARTIALLY ERODABLE SYSTEMS FOR TREATMENT OF OBSTRUCTIVE SLEEP APNEA
U.S. Pat. No. 8,167,787 dated May 1, 2012, PARTIALLY ERODABLE SYSTEMS FOR TREATMENT OF OBSTRUCTIVE SLEEP APNEA Other Publications Badin, P. & Serrurier, A. (2006). Three-dimensional linear modeling of tongue Articulatory data and models. Proceedings 7th Int. Seminar on Speech Production, ISSP7, pp. 395-40
Badin, P., Bailly, G., Reveret, L., Baciu, M., Segebarth, C., and Savariaux, C. (2002). "Three-dimensional linear articulatory modeling of tongue, lips and face; based on MRI and video images," J. Phonetics 30, 533-553.
Badin, P., Gabioud, B., Beautemps, D., Lallouache, T. M., Bailly, G., Maeda, S., Zerling, J. P. and Brock, G. (1995). Cineradiography of VCV sequences: articulatory-acoustic data for a speech production model. Proceedings of the 15th International Congress of Acoustics, vol. IV (pp. 349-352), Trondheim, Norway.
Block A J, Faukner J A, Huges R I., Remmers J E., Thach B T., Factors influencing upper airway closure. Chest 1984; 86: 114-122
Bothorel, A., Simon, P., Wioland, F. and Zerling, J.-P. (1986). Cineradiographie des voyelles et des consonnes du français. Institut de Phonétique, Université Marc Bloch, Strasbourg, France.
Buchaillard, S., Perrier, P., Payan, Y., 2009, "A biomechanical model of cardinal vowel production: muscle activations and the impact of gravity on tongue positioning," J. Acoust. Soc. Am., 126, pp. 2033 2051.
BUEHLER, W. J.—WANG, FREDERICK E.: A Summary of Recent Research on the NITINOL Alloys and their Potential Application in Ocean Engineering, Ocean Engineering, Vol. 1, 1967, pp. 105-120, Pergamon Press.
Bunton, K., and Weismer, G., 1994, "Evaluation of a reiterant force-impulse task in the tongue," J. Speech Hear. Res. 37, 1020-1031.
Chiel, H. J., Carago, P., Mansour, J., Hathi, K., 1992, "Biomechanics of a Muscular Hydrostat: A Model of Lapping by a Reptilian Tongue," Biol. Cybern., 67, pp. 403-415.
Dang, J. and Honda, K. (2004), "Construction and control of a physiological articulatory model," J. Acoust. Soc. Am. 115(2), 853-870.

Decker M J, Haaga J, Arnold J L, Atzberger D, Strohl K P. Functional electrical stimulation and respiration during sleep. J Appl Physiol 1993; 75: 1053-1061.

Douglas N J, Polo O. Pathogenesis of obstructive sleep apnoea/hypopnoea syndrome. Lancet 1994; 344: 653-655.

DUERING, T. W.-STOCKEL, D.-KEELEY, A.: Actuator and Work Production Devices, Engineering Aspects of Shape Memory Alloys, T. W. Duering, K. N. Melton, D. Stockel, and C. M. Wayman (eds), Butterworth-Helnemann, London, (1990) pp. 181-194. ISBN 0-750-61009-3.

Eastwood et al., 2003, Heterogeneous activity of the human genioglossus muscle assessed by multiple bipolar fine-wire electrodes, J Appl Physiol 94 1849-1858, 2003.

Edmonds L C, Daniels B K, Stanson A W, Sheedy P F, Shepard J W J. The effects of transcutaneous electrical stimulation during an awake state and sleep in patients with obstructive sleep apnoea. Am Rev Respir Dis 1992; 146: 1030-1036.

Eisele D W, Smith P L, Alam D S, Schwartz A R. Direct hypoglossal nerve stimulation in obstructive sleep apnoea. Arch Otolaryngol Head Neck Surg 1997; 123: 57-61.

Feldman A G. Once more on the Equilibrium-Point hypothesis (model) for motor control. *Journal of Motor Behavior.* 1986; 18(1):17-54.

GILL F. A.—PLANELL J. A.: In Vitro Thermomechanical Ageing of Ni—Ti Alloys, Journal of Biomaterial Application, 1998/12, pp. 237-248.

Guilleminault C, Powell N, Bowman B, Stoohs R. The effect of electrical stimulation on obstructive sleep apnoea syndrome. Chest 1995; 107: 67-73.

Guilleminault C, Tilkian A, Dement W C. The sleep apnea syndromes. *Ann Rev Med* 1976; 27:465-484

Hashimoto, K. and Suga, S. (1986), "Estimation of the muscular tensions of the human tongue by using a three-dimensional model of the tongue," J. Acoustic Soc. Japan 7(1), 39-46.

Kakita, Y., Fujimura, O., and Honda, K. (1985), "Computation of mapping from muscular contraction patterns to formant patterns in vowel space," in *Phonetic Linguistics*, edited by V. A. Fromkin (Academic, Orlando, Fla.), pp. 133-144.

Kiritani, S., Miyawaki, K. and Fujimura, O. (1976). A computational model of the tongue. *Annual Report of the Research Institute of Logopedics and Phoniatrics,* 10, 243-252, Tokyo University.

MIHÁLCZ I.—ILIE Z. E.: Using Electrical Resistance Variation of Shape Memory Alloys for Transformation Monitoring, 9th International DAAAM Symposium Intelligent Manufacturing, Automation and Networking, 22-24 Oct. 1998, Cluj-Napoca, Romania, pp. 215-216, ISBN 3-901509-08-9.

Miki H, Hida W, Chonan T, Kikuchi Y, Takishima T. Effects of submental electrical stimulation during sleep on upper airway patency in patients with obstructive sleep apnoea. Am Rev Respir Dis 1989; 140: 1285-1289.

Mortimore I L and Douglas N J, (1996), Genioglossus strength and fatiguability: relationship to apnea/hypopnea index. *Am J Respir Crit Care Med* 153: A532, 1996)

Napadow, Chen, Q., Wedeen, V. J., Gilbert, R. J., 1999, "Biomechanical Basis for Lingual Muscular Deformation During Swallowing," Am. J. Physiol., 277, pp. G695-701.

Napadow, V. J., Chen, Q., Wedeen, V. J., Gilbert, R. J., 1999, "Intramural mechanics of the human tongue in association with physiological deformations," Journal of Biomechanical Engineering. 32: 1-12.

Napadow, V. J., Kamm R., Gilbert R., 2002, "A Biomechanical Model of Sagittal Tongue Bending," Journal of Biomechanical Engineering, 124: 547-556

Odeh M, Schnall R, Gavriely N, Oliven A. Dependency of upper airway patency on head position: the effect of muscle contraction. Respir Physiol 1995; 100: 239-244

Odeh M, Schnall R, Gavriely N, Oliven A. Effect of upper airway muscle contraction on supraglottic resistance and stability. Respir Physiol 1993; 92: 139-150

Oliven A, O'Hearn D J, Boudewyns A, et al. Upper airway response to electrical stimulation of the genioglossus in obstructive sleep apnoea. J Appl Physiol 2003; 95: 2023-2029.

Oliven A, Schnall R P, Pillar G, Gavriely N, Odeh M. Sublingual electrical stimulation of the tongue during an awake state and sleep. Respir Physiol 2001; 127: 217-226.

Oliven et al. 2007, Effect of Genioglossus contraction on pharyngeal lumen and airflow in sleep apnoea patients, European Respiratory Journal, vol. 30 p. 1-11

Otsuka, K., Wayman, C. M., 1998. Shape Memory Materials. Cambridge University Press, New York Payan, Y. and Perrier, P. (1997), "Synthesis of V-V sequences with a 2D biomechanical tongue model controlled by the equilibrium point hypothesis," Speech Commun. 22(2-3), 185-205.

Perkell, J. S. (1974), "A physiologically oriented model of tongue activity in speech production," Ph.D. thesis, Massachusetts Institute of Technology, Boston, USA, Perkell, J. S. (1996), "Properties of the tongue help to define vowel categories: Hypotheses based on physiologically oriented modeling," J. Phonetics 24(1), 3-22.

Perkell, J. S. (1969). Physiology of speech production: results and implication of a quantitative cineradiographic study. Cambridge, Mass.: MIT Press.

Perrier, P., Payan, Y., Zandipour, M., and Perkell, J. S. (2003), "Influence of tongue biomechanics on speech movements during the production of velar stop consonants: A modeling study," J. Acoust. Soc. Am. 114(3), 1582-1599

Remmers, J. E., W. J. deGroot, E. K. Sauerland, and A. M. Anch. Pathogenesis of upper airway occlusion during sleep. J. Appl. Physiol. 44: 931-938, 1078

Saboisky Julian P., Jane E. Butler, Robert B. Fogel, Janet L. Taylor, John A. Trinder, David P. White, Simon C. Gandevial 2005, Tonic and phasic respiratory drives to human genioglossus motoneurons during breathing J Neurophysiol (Nov. 23, 2005). doi:10.1152/jn.00940.2005

Sanguineti, V., Laboissi`ere, R., and Ostry, D. J. (1998), "A dynamic biomechanical model for neural control of speech production," J. Acoust. Soc. Am. 103(3), 1615-1627

Schnall et al., 1995, Dilatory effects of upper airway muscle contraction induced by electrical stimulation in awake humans, J. Appl. Physiol. 78(5) 1950-1956

Schwab R J, Gupta K B, Gefter W B, Metzger L J, Hoffman E A, Pack A I. Upper airway and soft tissue anatomy in normal subjects and patients with sleep-disordered breathing: significance of the lateral pharyngeal walls. Am J Respir Crit Care Med 1995; 152:1673-1689

Schwartz A R, Eisele D W, Hari A, Testerman R, Erickson D, Smith P L. Electrical stimulation of the lingual musculature in obstructive sleep apnoea. J Appl Physiol 1996; 81: 643-652

Schwartz A R, ODonnell C P, Baron J, et al. The hypotonic upper airway in obstructive sleep apnea. Role of structures and neuromuscular activity. Am J Respir Crit Care Med 1998; 157: 1051-1057.

Sha et al., 2000, Force production of the genioglossus as a function of muscle length in normal humans; J. Appl. Physiol. 88: 1678-1684

Stone, M., Goldstein, M. H., and Zhang, Y. (1997). "Principal component analysis of cross sections of tongue shapes in vowel production," Speech Commun. 22, 173-184.

Takemoto, H., 2001, "Morphological analyses of the human tongue musculature for three-dimensional modeling," J. Speech Lang. Hear. Res. 44, 95-107.

Wade A J, Marbut M M, Round J M. Muscle fibre type and aetiology of obesity. Lancet 1990; 335: 805-808.

White D P. Pathogenesis of obstructive and central sleep apnea. Am J Respir Crit Care Med 2005; 172:1363-1370.

White D P. The pathogenesis of obstructive sleep apnoea: advances in the past 100 years. Am J Respir Cell Mol Biol 2006; 34: 1-6.

Wilhelms-Tricarico, R., 1995, "Physiological Modeling of Speech Production: Methods for Modeling Soft Tissue Articulators," J. Acoust. Soc. Am., 97, pp. 3085-3098.

Young T, Palta M, Dempsey J, Skatrud J, Weber S, Badr S. The ocurrence of sleep-disordered breathing among middleaged adults. N Engl J Med 1993; 328: 1230-1235.

Zienkiewicz, O. C., and Taylor, R. L. (1989). The Finite Element Method. Basic Formulation and Linear Problems. Maidenhead, UK (MacGraw-Hill, Maidenhead, UK).

What is claimed is:

1. A state changing actuator, arranged to be implantable at least in part helically into a tongue for treating obstructive sleep apnea, wherein the actuator comprises a helical section extending along a helix axis, the helical section of the actuator having compression and widening portions alternatingly provided along the helical section of the actuator,
   the helical section of the actuator being controllable between:
      a first state in which the helical section of the actuator has a relatively low stiffness to allow unhindered movement of the tongue when implanted; and
      a second state in which the helical section of the actuator has a higher stiffness than in the first state, and is deformed in such a way that the widening portions have moved inward towards the helix axis, as compared to the first state, and the compression portions have moved away from the helix axis, as compared to the first state; thereby deforming the tongue.

2. The actuator of claim 1, wherein the compression and widening portions are comprised in a deformable helical section defining a helical axis, and the actuator further comprising a force distributing section, and a torque producing section connecting the helical part and the force distributing section.

3. The actuator of claim 2, designed so to allow implanting the helical section in a patient's tongue for biasing the implant to deforming and stiffening the tongue body to a preferred shape without requiring tissue attachment; to allow the torque producing section leaving a root of the tongue; and to allow the force distributing section being place outside the tongue body.

4. The actuator of claim 3, wherein the force distribution section is arranged to be disposed between tongue root and geniohyoid, or between the geniohyoid and mylohyoid.

5. The actuator of claim 3, wherein the force distribution section is arranged as an attachable part, preferably arranged such that it is attachable to the hyoid bone or to the mandible bone.

6. The actuator of claim 3, wherein the force distribution part further comprises an axial compliant fin arranged to be positioned between the two geniohyoid muscles for preventing dislocation.

7. The actuator of claim 2, wherein a diameter of the helical section is between 3 mm and 20 mm.

8. The actuator of claim 2, wherein a pitch of the helical section is between 3 mm and 15 mm.

9. The actuator of claim 2, wherein the helical section comprises a fluid filled tube.

10. The actuator of claim 9, wherein the compression and widening portions are formed by relatively more rigid and less rigid portions comprised by the tube, such that variations in pressure of the fluid cause variations in deformation of the helical section about the helical axis.

11. The actuator of claim 10, wherein the more rigid portions comprise a spine portion on an inner side of the helical section towards the helical axis.

12. The actuator of claim 11, wherein the spine portion is selected from the group consisting of an increased tube wall thickness; a cable; a fibre; a belt.

13. The actuator of claim 11, further comprising more rigid and less rigid portions on a side of the helical section facing away from the axis, the portions formed as accordion bellows, such that when the side of the helical section facing away from the axis expands upon pressurization the actuator curves taking on a desired shape and capable of exerting a force on a second object when in a second pressurize state.

14. The actuator of claim 13, wherein the exerted force is arranged to vary along a length of the helical section by varying a wall thickness of the accordion bellows or a stiffness of the spine portion.

15. The actuator of claim 9, wherein the diameter of the tube is between 0.5 and 4 mm.

16. The actuator of claim 9, wherein the actuator comprises a protective second outer hull to contain fluid in case of internal rupture of the actuator.

17. The actuator of claim 9, wherein the tube is made of an elastomer, preferably a polymer, more preferably a fluoropolymer, such as FEP.

18. The actuator of claim 9, wherein the fluid comprises a saline fluid.

19. The actuator of claim 2, wherein the helical section comprises an electro-active polymer.

20. The actuator of claim 2, wherein the helical section comprises a ferromagnetic shape memory alloy or a temperature dependent shape memory alloy.

21. The actuator of claim 20, wherein the temperature dependent shape memory alloy comprises nitinol.

22. The actuator of claim 21, wherein the helical section comprises a nitinol tube enclosing an inner lead comprising an electrically conductive material, and a coating for electric insulation being disposed between the tube and the inner lead, wherein the tube and inner lead are electrical connected at a distal end of the helical section.

23. The actuator of claim 22, wherein the inner lead is made of a temperature dependent shape memory alloy.

24. The actuator of claim 22, wherein the inner lead is comprised of a plurality of leads electrically connected to the tube at different sections.

25. The actuator of claim 2, further comprising a flexible distal end section connected to the helical section, comprising a polymer fibre.

26. The actuator of claim 25, wherein a distal end of the distal end section has a substantially spherical shape, or has a conical form comprising a concave end arranged to face muscle fibres.

* * * * *